US008998808B2

(12) United States Patent
Wang et al.

(10) Patent No.: US 8,998,808 B2
(45) Date of Patent: Apr. 7, 2015

(54) SYSTEM FOR IDENTIFYING PATIENT RESPONSE TO ANESTHESIA INFUSION

(75) Inventors: Le Yi Wang, Novi, MI (US); Hong Wang, Novi, MI (US); Gang George Yin, Novi, MI (US)

(73) Assignee: Wayne State University, Detroit, MI (US)

( * ) Notice: Subject to any disclaimer, the term of this patent is extended or adjusted under 35 U.S.C. 154(b) by 2307 days.

(21) Appl. No.: 10/561,074

(22) PCT Filed: Jun. 21, 2004

(86) PCT No.: PCT/US2004/019971
§ 371 (c)(1),
(2), (4) Date: May 22, 2006

(87) PCT Pub. No.: WO2004/112603
PCT Pub. Date: Dec. 29, 2004

(65) Prior Publication Data
US 2007/0015972 A1 Jan. 18, 2007

Related U.S. Application Data

(60) Provisional application No. 60/479,937, filed on Jun. 19, 2003.

(51) Int. Cl.
*A61B 5/00* (2006.01)
*G06F 19/00* (2011.01)

(52) U.S. Cl.
CPC ........ *G06F 19/3468* (2013.01); *G06F 19/3481* (2013.01)

(58) Field of Classification Search
USPC ...................... 128/731, 923, 733; 395/22–24; 600/300–301, 544, 549; 703/11; 706/17
See application file for complete search history.

(56) References Cited

U.S. PATENT DOCUMENTS

| | | | | |
|---|---|---|---|---|
| 5,775,330 A * | 7/1998 | Kangas et al. | ................ | 600/544 |
| 5,964,713 A * | 10/1999 | Nomura et al. | ................ | 600/549 |
| 6,042,548 A * | 3/2000 | Giuffre | ........................ | 600/483 |
| 6,658,396 B1 * | 12/2003 | Tang et al. | ...................... | 706/17 |
| 7,693,697 B2 * | 4/2010 | Westenskow et al. | .......... | 703/11 |
| 2002/0173729 A1 * | 11/2002 | Viertio-Oja et al. | .......... | 600/544 |
| 2003/0055355 A1 * | 3/2003 | Viertio-Oja | ................... | 600/544 |
| 2004/0236188 A1 * | 11/2004 | Hutchinson et al. | .......... | 600/300 |

* cited by examiner

Primary Examiner — Bill Thomson
Assistant Examiner — Bobby Soriano
(74) Attorney, Agent, or Firm — Rohm & Monsanto, PLC

(57) ABSTRACT

A generic model structure captures basic characteristics in BIS-based patients' responses to anesthesia and surgical stimulation, the model being used in combination with the insight of an anesthesiologist. The model structure represents the patient response with a time delay, a time constant for response speed, and a nonlinear function for drug sensitivity. Clinical data confirms the model structure and is used to establish parameters and function forms for individual patients. A feedback and predictive control strategy for anesthesia drug infusion is then introduced on the basis of the patient model. Feedback control alone cannot avoid large fluctuations in BIS values when significant surgical stimulation is imposed, as a result of time delays in a patient's response to drug infusion. Predictive control attenuates fluctuations of BIS levels from surgical stimulation.

10 Claims, 27 Drawing Sheets

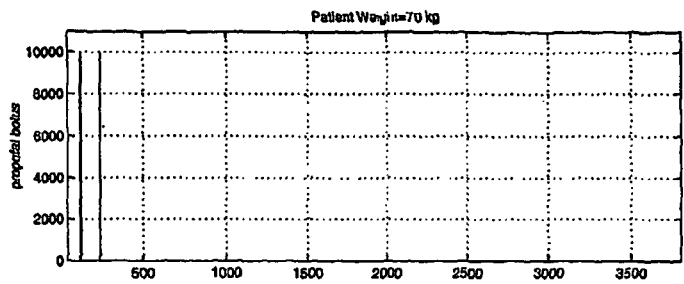
*Fig. 5a*
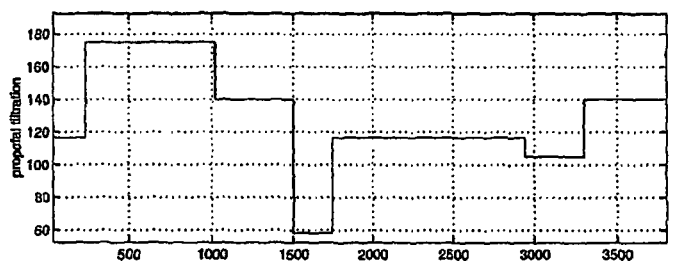
*Fig. 5b*
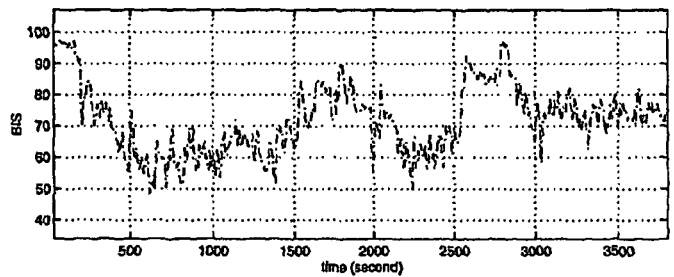
*Fig. 5c*
*Fig. 6*
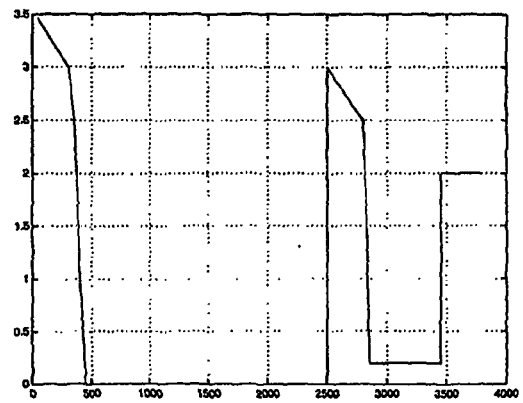

SYSTEM FOR IDENTIFYING PATIENT RESPONSE TO ANESTHESIA INFUSION

RELATIONSHIP TO OTHER APPLICATION

This application is a US national stage filing under 35 U.S.C. §371 of International Application No. PCT/US2004/019971 filed on Jun 21, 2004 and claims the benefit under 35 U.S.C. §119(e) of U.S. Provisional Patent Application Ser. No. 60/479,937 filed Jun. 19, 2003, the disclosure of which is incorporated herein by reference.

BACKGROUND OF THE INVENTION

1. Field of the Invention

This invention relates generally to systems for monitoring patients during infusion of anesthesia, and more particularly, to a model structure that captures basic characteristics in patients' responses to anesthesia and surgical stimulation, such as BIS-based responses.

2. Description of the Related Art

The goals of general anesthesia are to achieve hypnosis, analgesia, and patient immobility simultaneously throughout a surgical operation while maintaining the vital functions of the body. One of the most critical tasks of anesthesia is to attain an adequate anesthetic depth.

Traditionally, anesthesia depth has been deduced indirectly from physiological signals, including autonomic responses such as heart rate, blood pressure, tearing, and patient's movements in response to surgical stimulations. The BIS monitor, which is based on the bi-spectrum level of an EEG signal, provides a viable direct measurement of anesthesia depth. The BIS index ranges from 0 to 100, where 0 corresponds to a flat line EEG, and 100 is a fully awakened state. Deep sedation is present at 60 and below, where the patient does not respond to verbal stimulus and has low probability of explicit recall. As a result of this technological advance, there have been many attempts to apply control methodologies to assist or automate the drug infusion. These preliminary studies on computer-aided drug infusion have been developed with the use of simple control strategies such as fuzzy logic or lookup tables.

To facilitate further control strategy development for improved anesthesia performance, it is desirable to develop representative models of BIS responses to drug infusion. Such models will allow more substantial and faster development and testing of new control, signal processing and decision methodologies. Also, they will provide a non-risky platform to test performance, robustness, and safety under extreme conditions and rare events. A satisfactory modeling method for this application must address several unique and challenging issues. Unlike electrical, mechanical, and chemical processes that are often repeatable and data rich, patients differ dramatically in metabolism and pre-existing medical conditions, as well as their responses to the contemplated surgical procedures. Consequently, individualized models must be established for each patient with limited patient information and data points. The expert knowledge of anesthesiologists plays critical roles in predetermining patient response characteristics. Thus, there is a need for a model that is sufficiently simple for easy clinical utility, suitable for development and testing of control methods for improved performance, and capable of incorporating expert knowledge when the data are insufficient.

The research effort to develop computer-aided drug infusion systems has been both intensive and extensive since the early 1950s. The control methodologies employed include simple control (e.g., programmed control, relay control, and PID control), adaptive control (e.g., self-tuning control, self-organizing control, and dual mode controller), and intuitive or intelligent control (e.g., fuzzy control, neural network control, and expert system-based control). To measure anesthesia depth, many indices from the EEG signals have been proposed, including the median frequency, spectral edge frequency, and auditory evoked potentials. More recently, there have been provided in the art BIS monitors having claimed medical and economic benefits including reduction in hypnotic drug usage, earlier awakening, faster time to meet post-anesthesia care unit discharge criteria, better global recovery score, and more accurate assessment of awareness risk.

It is a great challenge to characterize mathematically a patient's response to drug infusion. As a result of large deviations in the aforestated physical conditioning, age, metabolism, pre-existing medical conditions, and responses to surgical procedures among various patients, there is a demonstrable high non-linearity and large variation in their responses to drug infusion. Physiology-oriented models are usually too complicated to establish individually using limited clinical data from a patient. On the other hand, anesthesiologists have been administering drug infusion successfully with only limited information on patients, such as weight and medical condition(s). The control strategies of an experienced anesthesiologist are based substantially intuitively on basic characteristics, such as the sensitivity of the patient to a drug infusion. There is, therefore, a need for a system that provides objective assistance to the anesthesiologist, thereby reducing the medical professional's reliance on subjective criteria.

It is, therefore, an object of this invention to provide a system that provides predictive information of a patient's response to anesthesia and surgical stimulation.

It is another object of this invention to provide a system that enables predictive control to compensate for surgical stimulation.

It is also an object of this invention to provide a system that provides visual indication of the predicted impact of a drug infusion decision on anesthesia depth and corresponding physiological variable.

It is a further object of this invention to provide a system that provides indication to an anesthesiologist of impact to the status of a patient that is anticipated from surgical stimulation from predetermined aspects of a surgical operation, such as incision and closing.

It is additionally an object of this invention to provide a system that signals to an anesthesiologist a warning of impending undesirable or critical patient conditions.

It is yet a further object of this invention to provide a system that utilizes real-time data in combination with the anesthesiologist's assessment to identify predetermined characteristics that are particular to a patient.

It is also another object of this invention to provide a system that facilitates optimization of drug dosage to achieve a desired patient status during surgery.

SUMMARY OF THE INVENTION

The foregoing and other objects are achieved by this invention which provides a knowledge-based and control-oriented modeling approach. The models retain only the key characteristics of patient responses that are essential for control strategy development and can be determined by either data or expert knowledge. The existing knowledge of anesthesiologists is abstracted and analyzed from their manual control methodologies. Time delay, response speed, and drug sensitivity turn out to be the key properties in this regard. This understanding is then used to develop a basic but flexible model structure. Its validity and clinical utility are verified by actual clinical data.

Although feedback control has been attempted in computer-aided or automated drug infusion, it will be shown herein that feedback control alone cannot avoid large fluctuations in BIS values when significant surgical stimulation is imposed. This drawback is largely due to the time delays in a patient's response to drug infusion. In this regard, predictive control becomes highly desirable. In predictive control, an early warning of predictable surgical stimulation such as incision will be sent to the control module. Based on an established model on the patient's response to the drug infusion and to the surgical stimulation, an advance adjustment of drug infusion rates (feed forward control) can be administered to compensate for the impact of the stimulation. As a result, the BIS value fluctuations can be greatly attenuated beyond the capability of a feedback system.

In accordance with a first method aspect of the invention, there is provided method of assisting a human expert in reducing predictable variations in the depth of anesthesia during the administration of a medical anesthesia drug to a patient. The method includes the step of solving:

$$y = f_p(x) = C_1 \frac{x}{x_1} \Phi_1(x) + C_2 \frac{x}{x_2} \Phi_2(x) + C_3 \frac{x}{x_3} \Phi_3(x)$$

where the coefficients $C_1$, $C_2$, $C_3$, as well as the time periods $\tau p$ (initial time delay after drug infusion) and $T_p$ (time constant representing speed of response) are initiated by assessment of a human expert.

In one embodiment of the invention, the human expert performs the step of assigning a relative value between 1 and 10 to represent the patient's response to infusion of the anesthesia drug, where 1 represents the slowest and 10 represents the fastest.

Typical set points are selected to be approximately $x_1 \cong 50$, $x_2 \cong 100$, and $x_3 \cong 150$.

In accordance with a further method aspect of the invention, there is provided a method of determining a model that corresponds to a predicted response of a patient to anesthesia drug delivery. The method includes the steps of:

first determining an initial time delay $\tau_p$ after drug infusion for the patient;

second determining a time constant $T_p$ representing speed of response of the patient; and third determining a nonlinear static function $f_p$ representing the sensitivity of the patient to a dosage of the anesthesia drug at steady state.

In one embodiment of this further method aspect of the invention, the steps of first, second, and third determining are implemented in a Weiner structure. In a further embodiment, the steps of first, second, and third determining are implemented in a Hammerstein structure.

In accordance with a system aspect of the invention, there is provided a system for determining a predicted response of a patient to the administration of an anesthesia drug. The system includes a first memory for storing patient dynamics information relating to the infusion of a bolus dosage of anesthesia drug, the first memory having a first output for producing a first output signal corresponding to a first anesthesia level. There is additionally provided a second memory for storing patient dynamics information relating to the infusion of a titrated dosage of anesthesia drug, the second memory having a second output for producing a second output signal corresponding to a second anesthesia level. A third memory stores patient dynamics information relating to the patient's predicted response to events of surgical stimulation, the third memory having a third output for producing a third output signal corresponding to an anesthesia effect level. A signal combiner arrangement receives the first and second output signals and the anesthesia effect level, and produces at an output thereof a combined anesthesia effect signal. A limiter is coupled to the output of the signal combiner for establishing maximum and minimum values of the combined anesthesia signal. Finally, a virtual anesthesia monitor produces an anesthesia value responsive to the combined anesthesia signal.

In one embodiment of this system aspect of the invention, the first, second, and third anesthesia levels correspond to respective BIS levels, the anesthesia effect level is a BIS level, and the combined anesthesia signal is a combined BIS level signal. In some embodiments, the virtual anesthesia monitor is a virtual BIS monitor for producing a BIS value responsive to the combined BIS signal.

In a further embodiment of this system aspect of the invention, there is provided a source of known unpredictable disturbances for producing an unpredictable disturbances signal, and the signal combiner arrangement is arranged to receive the unpredictable disturbances signal and the combined anesthesia effect signal is responsive to the unpredictable disturbances signal.

BRIEF DESCRIPTION OF THE DRAWING

Comprehension of the invention is facilitated by reading the following detailed description, in conjunction with the annexed drawing, in which:

FIGS. 5a to 5c are graphical representations of actual patient responses;

FIG. 6 is a graphical representation of scaled surgical stimulation levels;

DETAILED DESCRIPTION OF THE INVENTION

Figure 1:
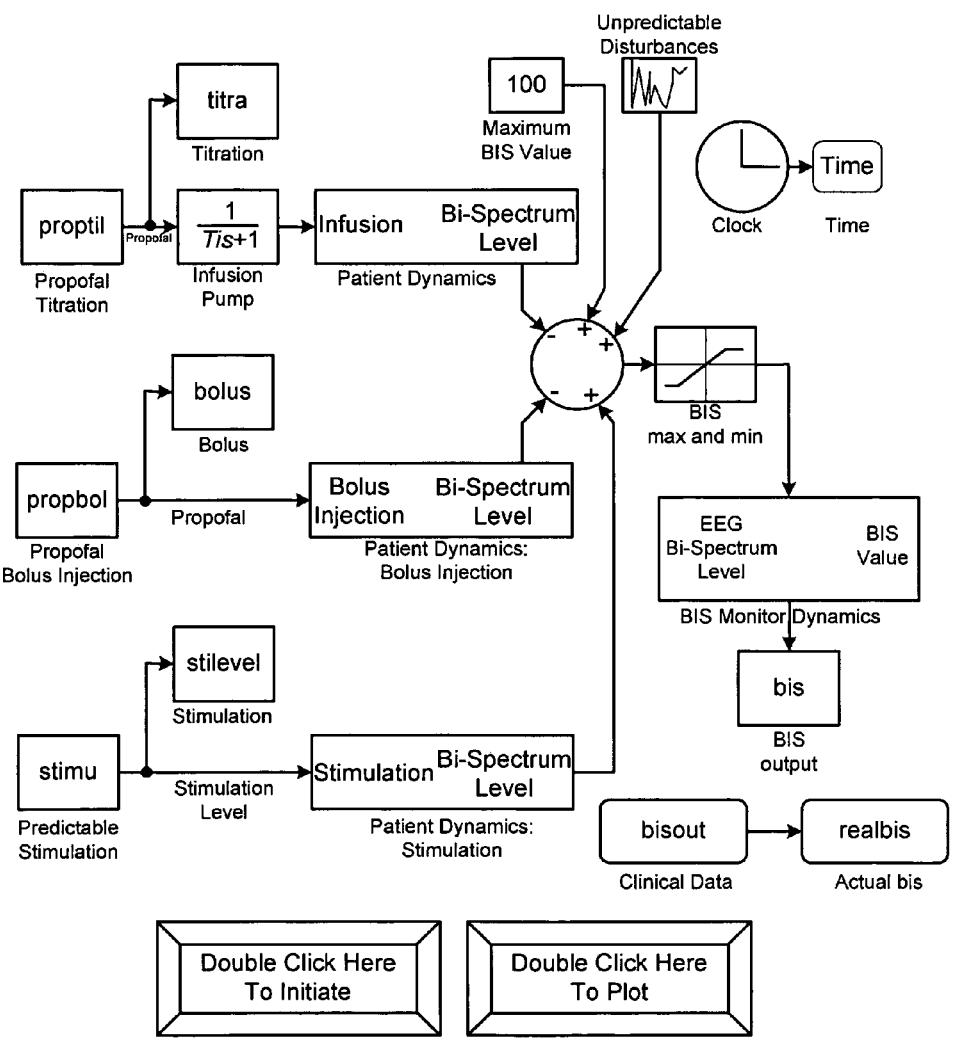
FIG. 1 is a block and line representation of a patient model structure in accordance with the present invention.

FIG. 1 is a block and line representation of a patient model structure in accordance with the present invention. The model contains three building blocks, each with a similar structure, as shown in FIG. 1. The first two blocks represent the patient response to propofol titration and bolus injection, respectively. The third block characterizes the patient response to predictable stimulation such as incision, closing, etc. For concreteness, it is assumed that propofol is the anesthesia drug although the model structure is generic and valid for other anesthesia drugs.

1. Model Structures of Patient Dynamic Responses to Drug Infusion and Stimulation The Titration Model Anesthesia drug titration, illustratively propofol titration, is administered in this specific illustrative embodiment of the invention by an infusion pump (Abbott/Shaw LifeCare™ Pump Model 4). The dynamic response between the titration command to the pump and the drug infusion rate at the needle point is represented by a first-order dynamic delay:

$$\frac{1}{T_i s + 1}$$

where $T_i$ is the time constant of the infusion pump. $T_i$ typically ranges from 0.2 to 2 seconds and can be predetermined from prior experiment data.

The key component of the present model is the patient dynamics. Although the actual physiological and pathological features of the patient will require models of high complexity, for control purposes it is not only convenient but essential to use simple models as long as they are sufficiently rich to represent the most important properties of the patient's response. Understanding the information used by anesthesiologists in infusion control, the patient's response to propofol titration is characterized with only three basic components:

(1) Initial time delay $\tau_p$ after drug infusion. During this time interval after a change of the infusion rate, the BIS value does not change due to time required for drugs to reach the target tissues and to complete volume distribution. This is represented by a transfer function $e^{-\tau_p s}$; (2) Time constant $T_p$ representing the speed of response. This reflects how fast the BIS value will change once it starts to respond. This is represented by the transfer function:

$$\frac{1}{T_p s + 1};$$

and (3) A nonlinear static function representing sensitivity of the patient to a drug dosage at steady state. This is represented by a function or a look-up table $f$.

Figure 2A:
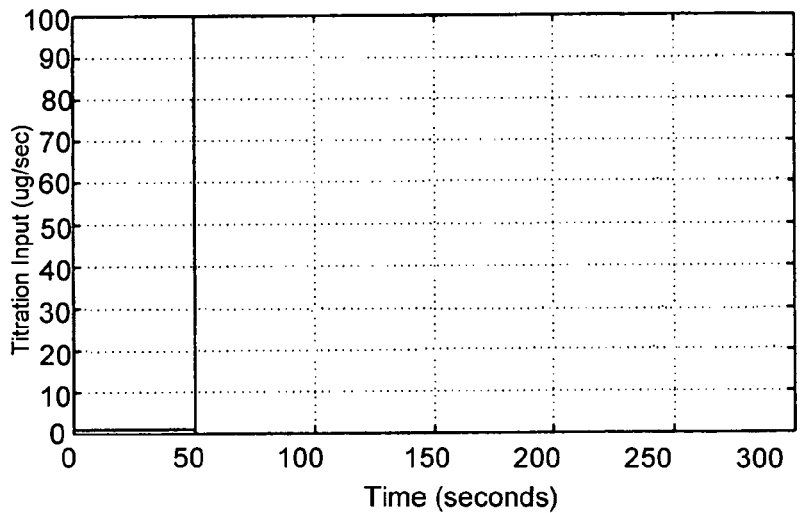
FIGS. 2a and 2b are graphical representations that are useful in characterizing a titration model aspect of the invention.
Figure 2B:
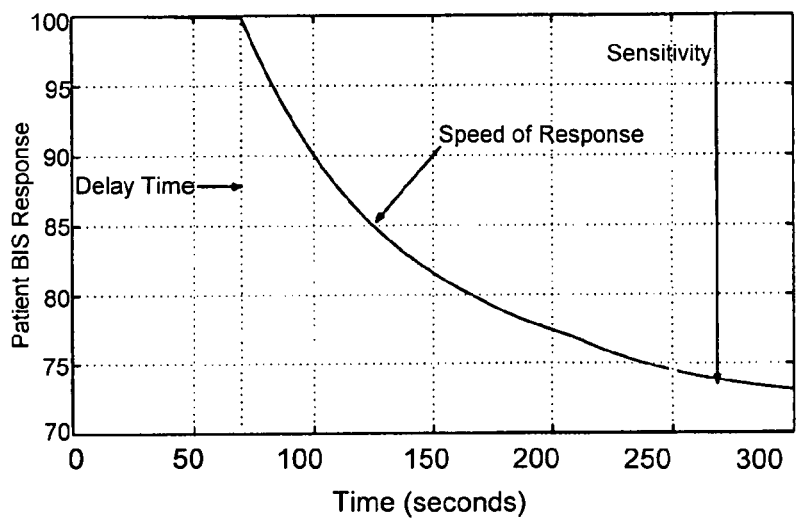

FIGS. 2a and 2b are graphical representations that are useful in characterizing a titration model aspect of the invention. The meanings of the three above-mentioned basic components are depicted in FIGS. 2a and 2b. Consequently, a model structure for titration is shown in FIG. 3.

Figure 3:
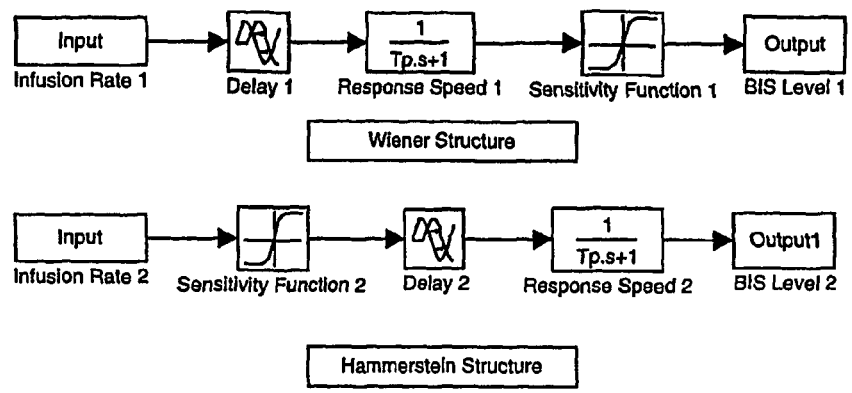
FIG. 3 is a block and line representation of a titration model structure.

FIG. 3 is a block and line representation of a titration model structure. The top portion of the figure is the Wiener structure in which the nonlinear function follows the linear part; the bottom portion of the figure is the Hammerstein structure in which the nonlinear function precedes the linear part. Both can used in this application. For concreteness, we will use the Wiener structure in this paper. The delay time $T_d$, time constant $T_p$ and the sensitivity function of the model vary dramatically among patients and must be established individually for each patient. Model development using clinical patient data will be detailed hereinbelow.

Bolus Injection Model

Bolus injection inputs a large amount of drug in a short time interval. The bolus model has a structure similar to the titration model. However, due to the highly nonlinear nature of the patient response, it has been observed that the patient response to bolus injection demonstrates different model parameters. The dynamic part is represented by a transfer function $$e^{-\tau_{bolus} s} \frac{1}{T_{bolus} s + 1}.$$

Data analysis indicates that bolus injection response has a slightly shorter delay time due to an increased speed for drug to reach the target tissues. However, its time constant is much larger. Also, its residue impact on the BIS values is small at steady state. This results in a very different sensitivity function, which will be detailed in the next section.

Surgical Stimulation

One of the most important control tasks in infusion control is to predict the impact of surgical stimulation on the BIS levels. Surgical stimulation is a main cause of large fluctuations in anesthesia depth during a surgical procedure. Early prediction of the impact will allow advance drug adjustment before a feedback signal from the BIS monitor activates control actions. Typical surgical stimulation includes initial preparation, incision, closing, etc. Such stimulations cause large fluctuations in BIS values and must be compensated by adjusting anesthesia drugs. An experienced anesthesiologist understands the level of such stimulation and adjusts drugs in advance to minimize its impact.

Surgical stimulation has an opposite impact on the BIS values to the drug infusion. The higher the stimulation, the higher the BIS value. The sensitivity of the BIS values to stimulation decreases with deepening of anesthesia, i.e., lower BIS values. Unlike drug infusion whose rates can be controlled and measured, stimulation is not controlled by anesthesiologists and cannot be accurately measured. On the other hand, unlike unpredictable disturbances or noises, significant surgical stimulation is predictable in advance and can be roughly characterized by their severity in affecting BIS values.

Classification levels from 1 to 5 to represent the severity of the stimulation: 1 being a minor stimulation and 5 the most significant stimulation. For control purposes, these rough characterizations are clinically feasible and sufficient for predictive control, which will be described in detail hereinbelow (see, Predictive Control). Patient responses to surgical stimulation are represented by the third model block. The block contains also a time delay $\tau_s$ and a transfer function:

$$\frac{1}{T_s s + 1}$$

to reflect its dynamics and a lookup table for its impact on the BIS levels at the steady state. Since a patient's BIS sensitivity to stimulation depends on hypnosis state, a scaling factor $\alpha$ is introduced. $\alpha$ takes values between 0 and 1. The surgical stimulation is first scaled by:

Stimulation Level×$\alpha$=Scaled Stimulation Level

The scaled stimulation is then used to predict the impact on the BIS measurements. A typical curve of $\alpha$ as a function of the BIS value is depicted in FIG. 4.

Figure 4:
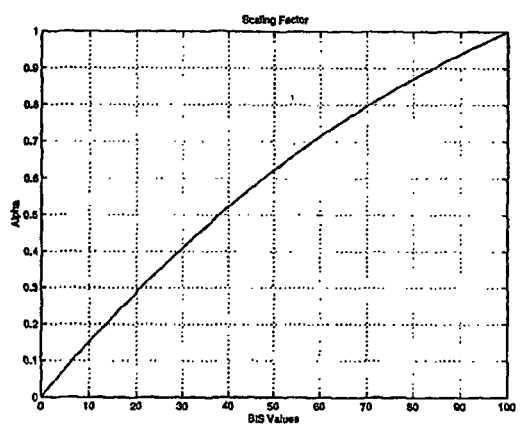
FIG. 4 is a is a graphical representation that shows the relationship between a scaling factor and a BIS value.

FIG. 4 is a is a graphical representation that shows the relationship between a scaling factor and a BIS value. Information on an upcoming stimulation will be used as a prewarning to provide a predictive control so that the impact of the stimulation can promptly be compensated by early tuning of drug infusion.

BIS Monitor Dynamics

The BIS monitor measures the EEG signals and performs bi-spectrum statistical analysis. Due to the processing time and data windows required in this procedure, the BIS monitor introduces a pure time delay (from processing time) and a dynamics delay (related to the size of data windows). Its relevant dynamics for effecting control can be represented by a system transfer function:

$$e^{-\tau_b s} \frac{1}{T_b s + 1}$$

cascaded with a nonlinear limiter with lower limit 0 and upper limit 100 (defining the BIS range). BIS monitor dynamics can be established off-line, independent of surgical procedures.

Other Disturbances

There are many sources of disturbances that will also affect the BIS readings. These include unpredictable stimulation to the patient, electrical noises, sensor attachment movements, environment noises, etc. These disturbances are unpredictable and cannot be compensated by early predictive control. Their impact on BIS levels will be minimized by a feedback action.

Model Verification and Development by Clinical Data

Data Collection Protocol

To verify the utility of the model structure and develop individual patient models, clinical data are collected, after an approval from the IRB board. In the clinical data collection process, standard medical care is given to the patients without any deviations. A typical protocol is described in the following: The BIS monitor is applied. After the monitor sustains a base level of the BIS values, versed (a drug) and fentanyl are given for inducing preoperative sedation and controlling a BIS level higher than 90. After the patient is brought into the operating room, other physiological parameters will be monitored, such as blood pressure, EKG, pulse oximeter, and end-tidal $CO_2$ (after administering oxygen). Sedation will start with 1 mg versed and bolus propofol injection of 20 mg IV, followed by propofol infusion of initial rate 25 mg/kg-min to control the BIS level to the range of 70-85. Before surgical incision, 50 mg of fentanyl is given and propofol infusion rate is adjusted to control the BIS level to 50-65. After incision, fentanyl and propofol are continuously adjusted to maintain the BIS level at 60-75 until the end of the surgery. When the surgical closing starts, the BIS level is adjusted to 70-85 until the end of anesthesia drug administration.

Actual drug infusion rates and BIS trajectories vary with surgical procedures. Drug infusion rates are manually recorded. BIS trajectories are recorded in the monitor and transferred to a laptop computer using the standard HyperTerminal software. The data are then translated into Matlab™ data files for further data processing.

Clinical Data and Analysis

One typical data set is used in the following subsections to illustrate the modeling process and verification results. In this case, the anesthesia process lasted about 76 minutes, starting from the initial drug administration and continuing until last dose of administration. Propofol was used in both titration and bolus. Fentanyl was injected in small bolus amount three times, two at the initial surgical preparation and one near incision. Analysis shows that the impact of fentanyl on the BIS values is minimal. As a result, it is treated as a disturbance and not explicitly modeled in the present example. The drug infusion was controlled manually by an experienced anesthesiologist. The trajectories of titration (in μg/sec) and bolus injection (converted to g/sec) during the entire surgical procedure were recorded, which are shown together with the corresponding BIS values in FIGS. 5a to 5c, which are graphical representations of actual patient responses.

The patient was given bolus injection twice to induce anesthesia, first at t=3 minute with 20 mg and then at t=5 minute with 20 mg. They are shown in the figure as 10000 μg/sec for two seconds, to be consistent with the titration units. The surgical procedures were manually recorded. Three major types of stimulation were identified: (1) During the initial drug administration (the first 6 minutes), due to set-up stimulation and patient nervousness. This is characterized as a level 3-3.5 stimulation by the anesthesiologist. (2) Incision at t=45 minutes for about 5 minutes duration. This is characterized as a level 5 stimulation. (3) Closing near the end of the surgery at t=60 minutes. This is characterized as a level 3.5 stimulation. Due to different BIS values in these time intervals, the scaling factor a has different values under these three types of stimulation. The scaled stimulation level trajectory is shown in FIG. 6, which is a graphical representation of scaled surgical stimulation levels.

Model Development

The data from the first 30 minutes are used to determine model parameters and function forms. The infusion pump model and the BIS monitor model can be derived or identified with limited impact from real data. For the systems used in this study, the time constant for the infusion pump model is estimated as $T_I$=0.5 second. The delay time and time constant of the BIS monitor depend on the setting. For a short window selection (for fast response), these parameters are estimated as $\tau_b=10$ seconds and $T_b=10$ seconds.

Figure 7:
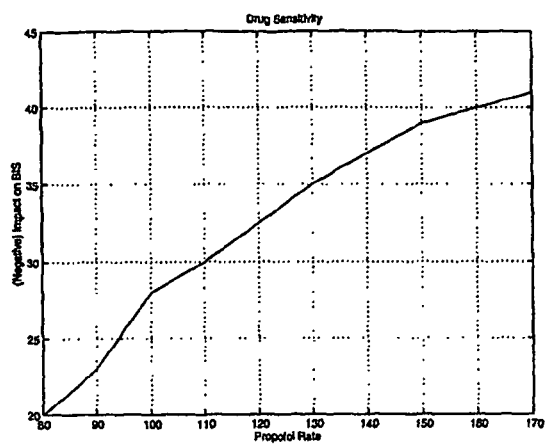
FIG. 7 is a graphical representation of a drug sensitivity function (titration)

For estimating the parameters in the titration block, the data in the interval where the bolus and stimulation impact is minimal (between t=10 to t=30 minutes) are used. By optimized data fitting (least-squares), the estimated parameter values $\tau_p=10$ second and $T_p=90$ second are derived. The data-generated sensitivity function is shown in FIG. 7 which is a graphical representation of a drug sensitivity function (titration).

Figure 8:
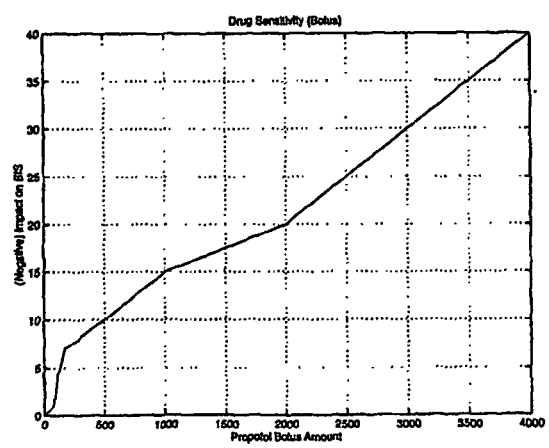
FIG. 8 is a graphical representation of a drug sensitivity function (bolus)
Figure 9:
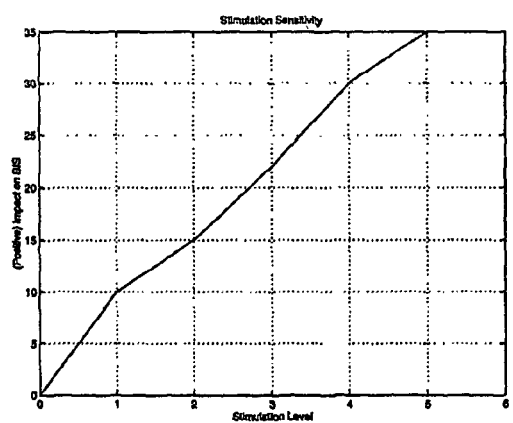
FIG. 9 is a graphical representation of a stimulation sensitivity function.
Figure 10A:
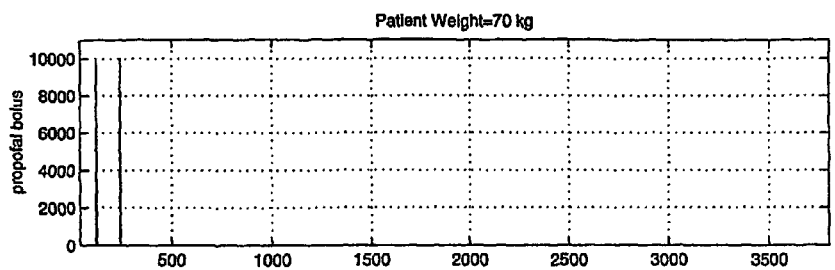
FIGS. 10a to 10d are graphical representations of patient model responses.
Figure 10B:
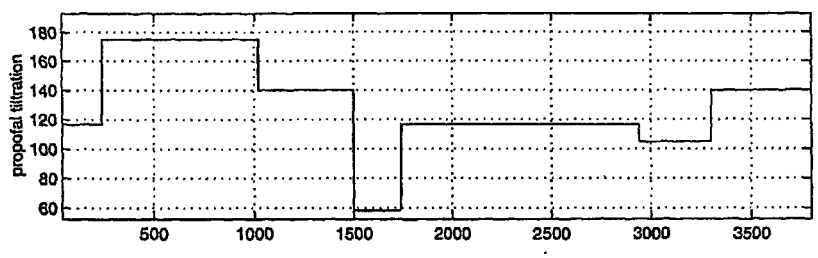
Figure 10C:
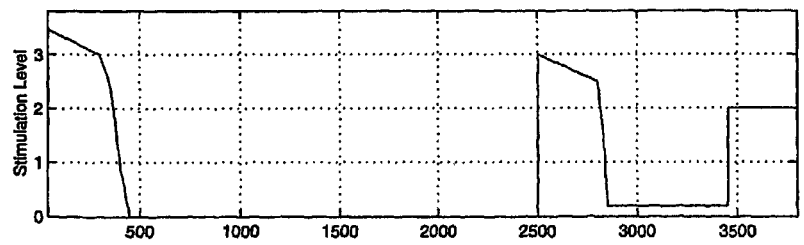
Figure 10D:
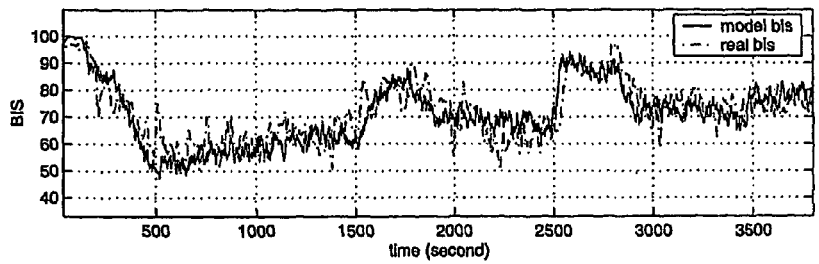

The first interval of data is then used to estimate the bolus model and stimulation model. The data are first processed to remove the impact of titration by using the titration model developed above. The processed data are then used to determine model parameters and function forms. The resulting parameters are (all in seconds): $\tau_{bolus}=10$, $T_{bolus}=250$, $\tau_s=12$, $T_s=3$, $K_s=4$. The sensitivity functions are shown in FIG. 8, which is a graphical representation of a drug sensitivity function (bolus), and in FIG. 9, which is a graphical representation of a stimulation sensitivity function.

Verification

The actual BIS response is then compared to the model response over the entire surgical procedure. Comparison results are illustrated in FIGS. 10a to 10d, which are graphical representations of patient model responses. Here, the inputs of titration and bolus are the recorded real-time data. The model output represents the patient response very well. In particular, the model catches the key trends and magnitudes of the BIS variations in the surgical procedure. This indicates that the model structure contains sufficient freedom in representing the main features of the patient response. Also, the impact of surgical stimulation is captured by the model. These features are of essential importance in designing control strategies for computer-aided drug infusion.

Feedback Control

Based on the patient model established hereinabove (Model Structures of Patient Dynamic Responses to Drug Infusion and Stimulation), a control strategy is described for maintaining BIS levels and to provide robustness. The control consists of two elements: (1) a feedback part for fine tuning titration to compensate BIS deviations due to drifting of patient dynamics, unpredictable disturbances and noises, model errors due to simplification and non-linearity; and (2) a predictive control to provide fast compensation for large but predictable stimulation.

To justify the utility of this control structure, there is first presented a discussion on feedback control and its performance.

Feedback Control

Figure 11:
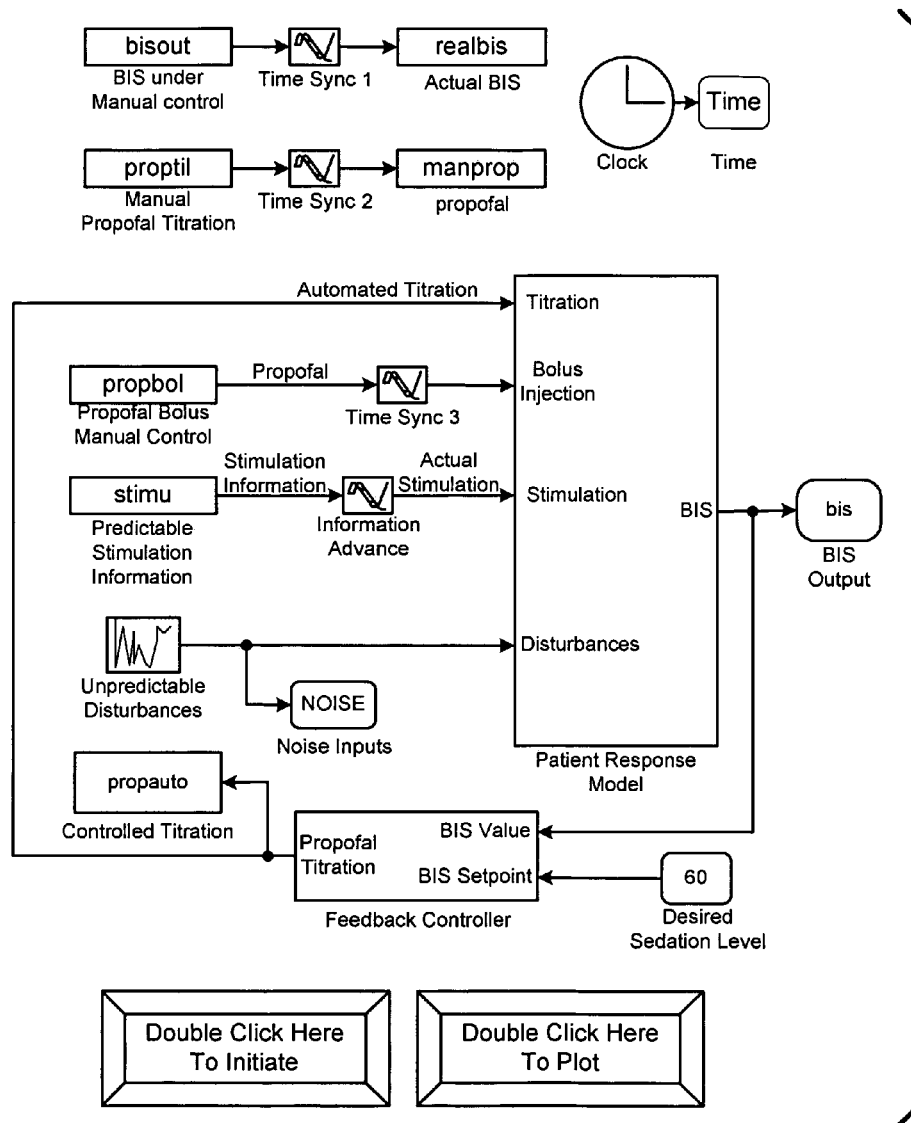
FIG. 11 is a block and line representation of a feedback only control arrangement.

Feedback control relies on the measured BIS signal to activate control actions in order to attenuate BIS deviations due to disturbances and stimulation. In feedback control, even the predictable stimulation will be considered as disturbances to the system. The structure of feedback-only controllers is depicted in FIG. 11, which is a block and line representation of a feedback only control arrangement.

It has been learned from multiple studies of feedback controllers for use in anesthesia drug control that the highly nonlinear nature of the patient response precludes the direct application of linear control theory. Some controller types that can be tuned for nonlinear systems include PD, fuzzy, etc. In the present embodiment, a typical PID controller employed to investigate feedback performance.

Figure 12:
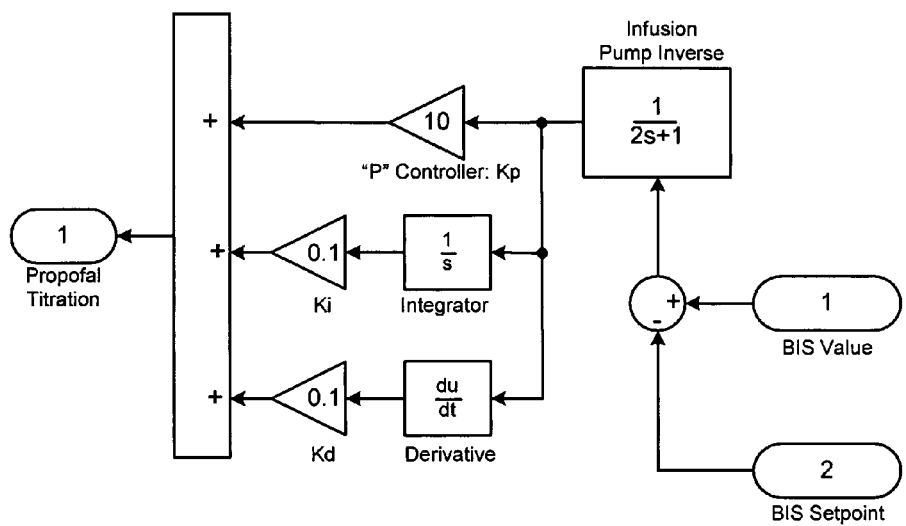
FIG. 12 is a block and line representation of a PID controller.
Figures 13A, 13B, 13C, 13D, 13E:
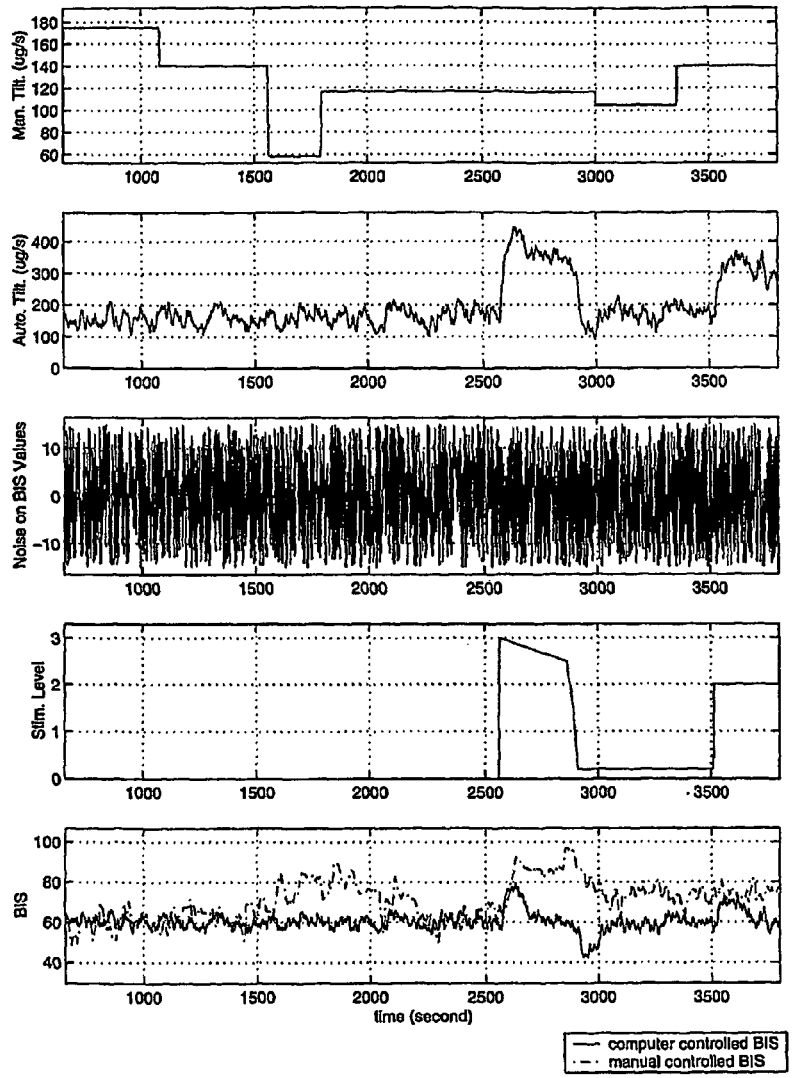
FIGS. 13a to 13e are graphical representations showing the quality of the feedback control.

The PID controller is illustrated as a block and line representation in FIG. 12. The parameters $K_p$, $K_i$, and $K_d$ are design parameters. It is well understood that choosing these parameters is subject to fundamental tradeoffs. For instance, large $K_p$ will result in oscillations, while small $K_p$ will result in a large control error. Similarly, large $K_d$ will amplify noises. Fine tuning of the parameters along these principles has resulted in the control parameters indicated in the figure.

Performance Analysis and Fundamental Limitations

FIGS. 13a to 13e, which are graphical representations show the quality of the feedback control performance. A careful examination of the BIS trajectory reveals that the feedback control is very effective in attenuating BIS deviations due to random noises (see the portion of FIG. 13d where no large surgical stimulation exist). This observation indicates that feedback control design for attenuation of random or small disturbances in this application is not particularly difficult, even though the system is highly nonlinear. This is consistent with other reports on BIS-based closed loop anesthesia control. However, in the presence of large surgical disturbances, performance deteriorates very rapidly. This is clearly reflected at the time intervals where incision and closing occur. This phenomenon is of generic nature. One explanation for this phenomenon is that the BIS values respond to surgical stimulation faster than to drug infusion. As a result, there is a feedback loop time in which the influence of the stimulation is not compensated, regardless the control algorithms. Furthermore, the commonly used method of relying on the BIS output speed to accelerate control actions in the event of stimulation cannot be effectively used in this application. This is due to the fact that the BIS measurements are derived from EEG signals, which contain a lot of high frequency noises. Acceleration of feedback will cause amplification of noises. Consequently, improved control strategies are needed beyond pure feedback control, as will be described below.

Predictive Control

Design and Performance

It is observed from clinical data that it typically takes a delay time of 5-20 seconds before the BIS value changes after a modification to the titration rate. The BIS value changes gradually thereafter with a time constant 80-200 seconds. On the other hand, a surgical stimulation impacts the BIS levels much faster. Consequently, a surgical stimulation will inevitably cause large deviations on the BIS values if the control action depends solely on the BIS monitor. This will significantly compromise the quality and safety of the anesthesia care of the patient. Such large deviations are evident from the manual controlled BIS trajectory in FIG. 10. For example, the BIS level rises to 90 after incision, which is highly undesirable. From a control viewpoint the only remedy is to provide preventative drug infusion in prediction of a significant stimulation. This becomes the main goal of the predictive control block.

Figure 14:
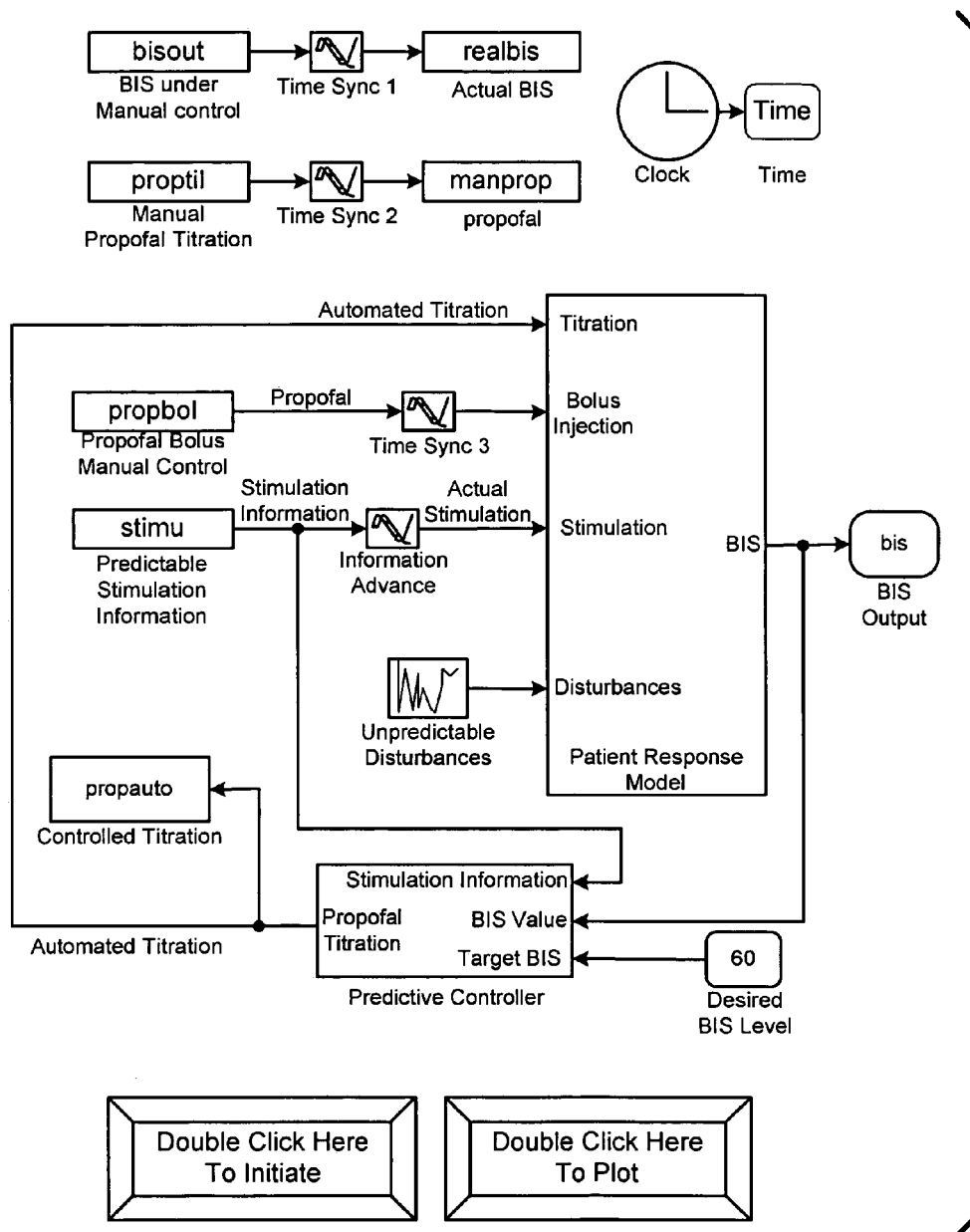
FIG. 14 is a block and line representation of a control arrangement.

The control structure is depicted at a high level in the block diagram of FIG. 14, which is a black and line representation of a control arrangement. It is noted that predictable stimulation is distinguished from noises. In accordance with the present control strategy, the adverse effects of noises are diminished by feedback control and predictable stimulation and are compensated by predictive control algorithms. Information on predictable stimulation is sent in advance to the control module.

Figure 15:
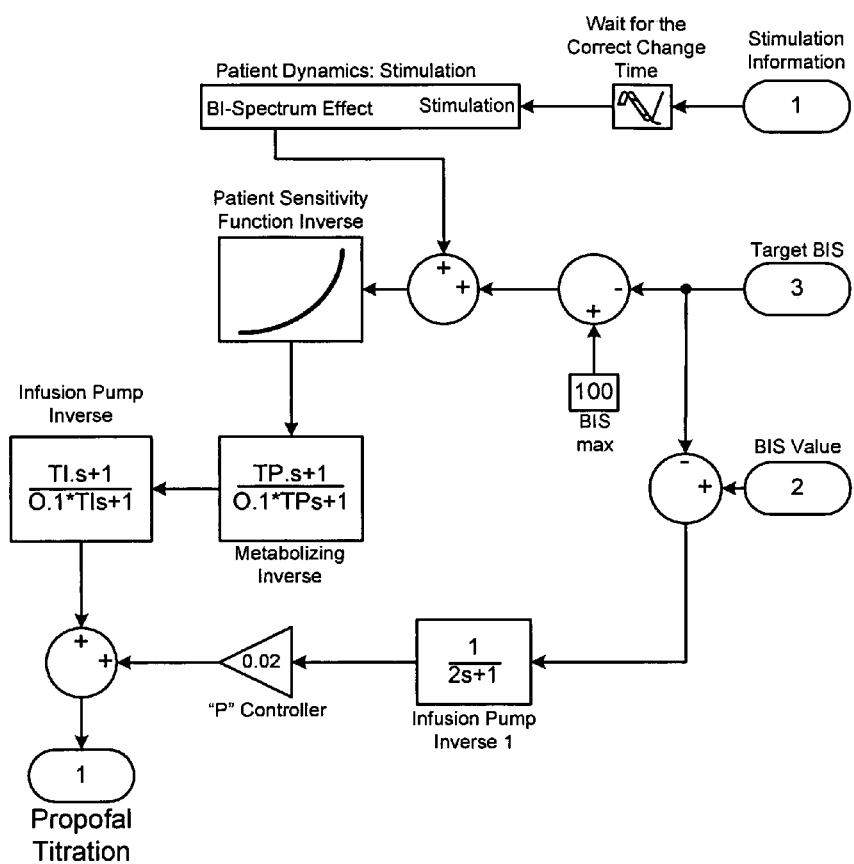
FIG. 15 is a block and line representation of a predictive and feedback control arrangement.
Figures 16A, 16B, 16C, 16D, 16E:
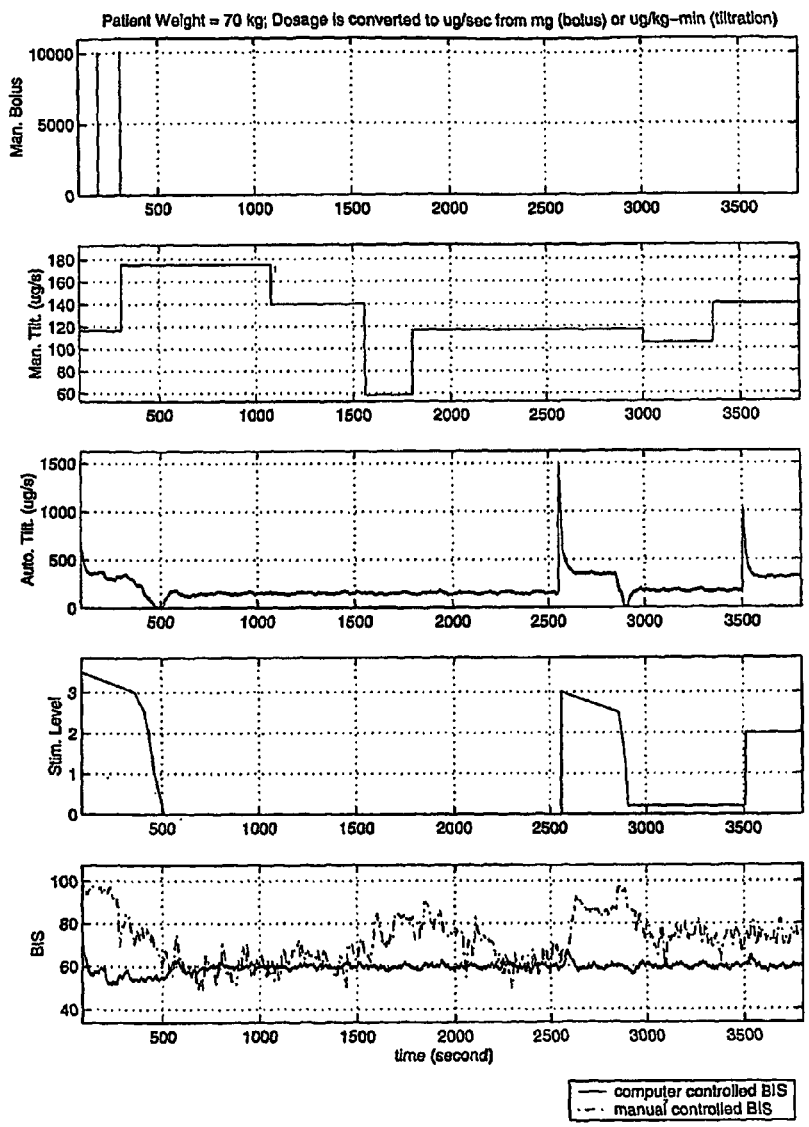
FIGS. 16a to 16e are graphical representations showing the control quality.

FIG. 15 is a block and line representation of a predictive and feedback control arrangement showing a detailed control structure. For the patient characteristics under consideration, a simple feedback structure appears sufficient. Here, there is employed a basic proportional feedback ($K_p$=10, the same as in the feedback-only control) together with a filter that compensates infusion pump dynamics. The predictive control block is significantly more involved. It is designed on the basis of optimal stable inversion of the patient dynamic models. In principle, the desired drug infusion rates under a given stimulation can be estimated by inverting the patient model. However, such an inversion will result in a non-causal and unstable system, and hence is not acceptable. The task here is to find a causal stable (nonlinear) system that can optimally approximate the model inverse in the frequency band of interest. A computer program to find such an optimal system is then devised.

To understand the potential benefits and limitations of the control strategy, we applied it to the patient model. The BIS trajectories from manual control are compared to those from feedback and predictive control. The simulation results are presented in FIGS. 16a to 16e, which are graphical representations showing the control quality. Due to its predictive capability and robustness in compensating BIS deviations continuously, BIS levels can be maintained much more steadily under the computer control strategy.

It should be emphasized, however, that if stimulation is not well predicted, then control quality will deteriorate. On the other hand, even incomplete information on the upcoming stimulation can be used to improve BIS fluctuations.

Robustness Against Modeling Errors

Since a patient model characterizes only the key features of the patient response, it is only an approximation of the actual patient response. As a result, it is essential that the control strategies remain functional under modeling errors and inaccuracy in defining stimulation levels and scaling factors. The inventors herein have tested the robustness of this control structure by introducing many variations of potential modeling errors and perturbed stimulation characterizations. The predictive plus feedback control structure provides satisfactory performance under these perturbations. The actual testing results are omitted here for simplicity.

Modules and Learning Functions

Figure 17:
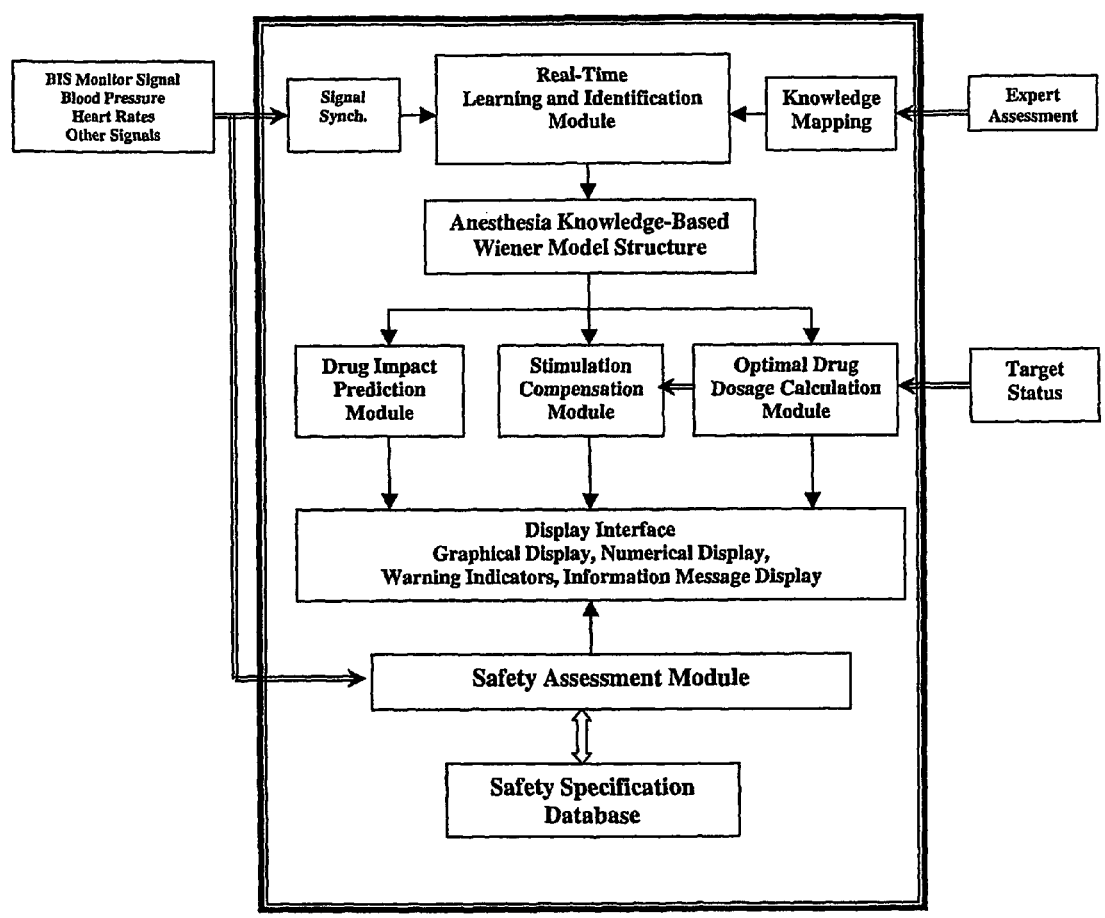
FIG. 17 is a block and line representation of a system configuration showing certain ones of the modules.

FIG. 17 is a block and line representation of a system configuration showing certain ones of the modules. As shown in this figure, a plurality of signals, that may, in certain embodiments of the invention, include the BIS monitor signal, a blood pressure signal, a heart rate signal, and other signals is delivered simultaneously to a Real-time Learning and Identification Module after signal synchronization and to a Safety Assessment Module that compares the signal values to predetermined safety specifications stored in a database. The result of the safety assessment is displayed on a Display Interface. As shown, the Display Interface includes graphical and numerical displays, as well as warning indicators and messages.

The Real-time Learning and Identification Module additionally receives information responsive to the assessment by an expert (i.e., an anesthesiologist) that has been processed by a Knowledge Mapping Module. The output of the Real-time Learning and Identification Module is conducted to an Anesthesia Knowledge-based Wiener Model Structure, that functions as hereinabove described.

Data corresponding to a desired target status for the patient (not shown) is delivered to an Optimal Drug Dosage Calculation Module that also receives the data from the Anesthesia Knowledge-based Wiener Model Structure. The status of the Optimal Drug Dosage Calculation Module is displayed on the Display Interface, and the corresponding data is delivered to a Stimulation Compensation Module that also receives the data from the Anesthesia Knowledge-based Wiener Model Structure. The data from the Stimulation Compensation Module is displayed. In addition, the data from the Anesthesia Knowledge-based Wiener Model Structure is delivered to a Drug Impact Prediction Module, the output of which is also displayed.

Figure 18:
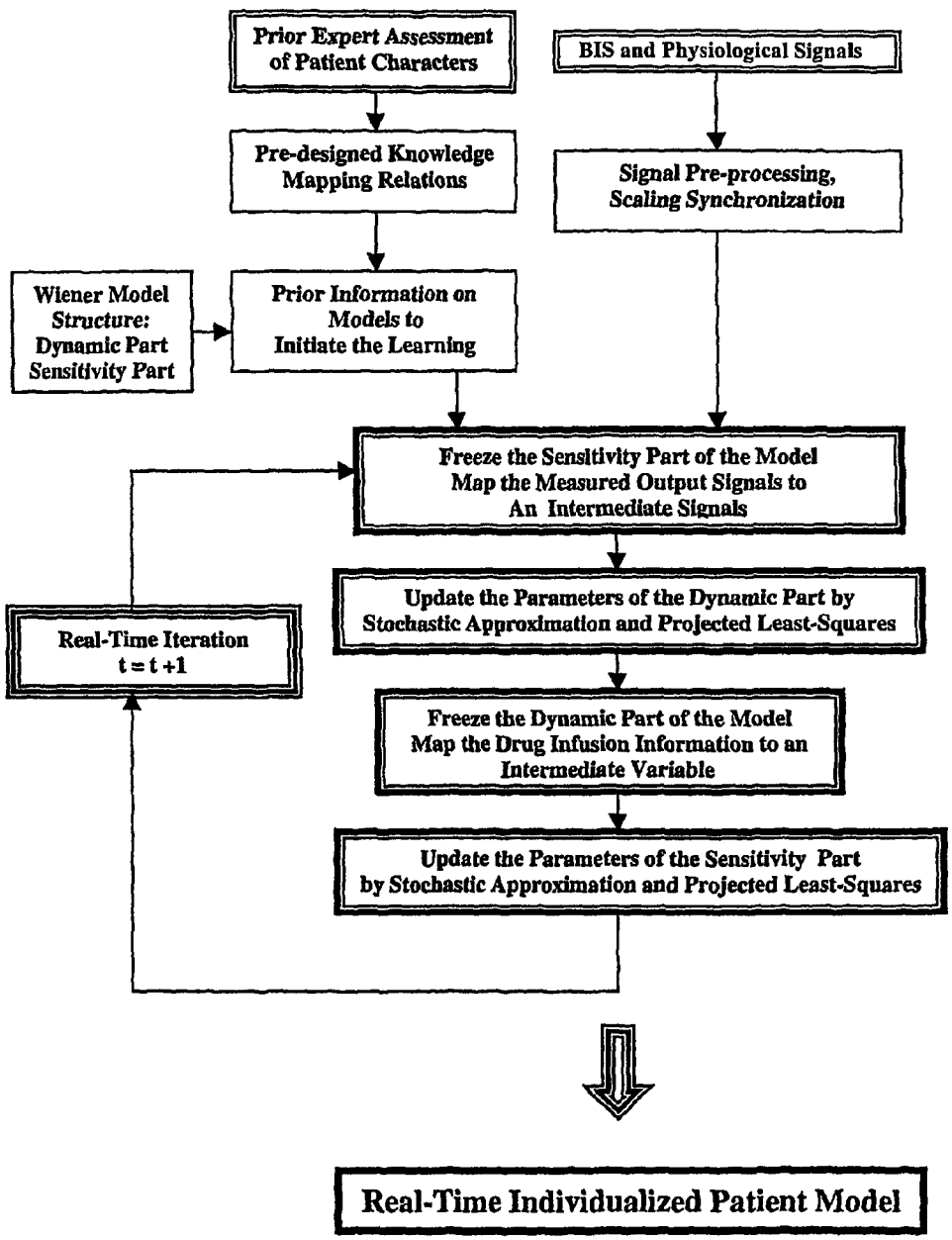
FIG. 18 is a block and line representation showing the core learning functions.

FIG. 18 is a block and line representation showing the core learning functions and their interrelationship in a specific illustrative embodiment of the invention. As is seen in this figure, two forms of input data (i.e., expert assessment and BIS and physiological data) are processed and delivered to an iterative process.

The prior expert assessment data is organized in accordance with a predetermined knowledge mapping relationship and combined with the dynamic and sensitivity processing of the Weiner model to form a body of prior information. This prior information is then delivered to the first stage of the iterative process where the sensitivity portion of the model map data is captured. Simultaneously, the BIS and physiological data is processed, scaled, and synchronized, and is also delivered to the first stage of the iterative process.

In this specific illustrative embodiment of the invention, the output of the first stage of the iterative process is delivered to a second stage, where the parameters of the dynamic portion of the model map is updated by stochastic-approximation and projected least squares processes. The resulting data then is delivered to the third stage of the iterative portion of the process where the dynamic portion of the model map is captured and an interim item of drug infusion data is developed. The interim item of drug infusion data then is delivered to the fourth stage of the iterative portion of the process where the parameters of the sensitivity portion of the model map are updated by stochastic approximation and projected least squares processes. This process then is repeated by real-time iteration where t=t+1, until an adequate Real-Time Individualized Patient Model is formed.

The mathematical underpinnings of these processes is described below.

Expert Knowledge and Fast Identification

The patient model must be individually developed to accommodate differences in patient characteristics, pre-existing medical conditions, surgical types, and other deviations. Since anesthesia infusion decisions must be made before substantial data are available, it is imperative that prior expert knowledge of an anesthesiologist is incorporated into the learning process. In this section, a basic identification method will first be developed. Some essential properties of the method will be established. It will then be applied to real clinical data in the subsequent sections.

Systems and Expert Information

The system under consideration has a Wiener structure with input u and output y:

$$x = Gu + \tilde{w}, \quad y = f(x) + \tilde{v}$$

where G is a dynamic linear system, $f$ is a memoryless nonlinear function, and $\tilde{w}$ and $\tilde{v}$ are random noises. In our applications here, G and $f$ represent the dynamic (or transient) and steady-state behavior of a patient's response to a drug infusion input, respectively. Simple examples of G include $$G(s) = \frac{1}{1+T_s}(\theta = T) \text{ or } e^{-\tau s}\frac{1}{1+Ts}(\theta = [\tau, T]').$$

Here and henceforth, for a vector or matrix z, z' denotes its transpose. In our algorith, for computerized data processing, G will be discretized and represented by an ARMA (Auto-Regression and Moving Average) model $$x_k = -a_1 x_{k-1} - \ldots - a_n x_{k-n} + b_0 u_k + b_1 u_{k-1} + \ldots + b_n u_{k-n} +$$
$$\tilde{w}_k = \phi'_k \theta + \tilde{w}_k$$

where $$\phi'_k = [-x_{k-1}, \ldots, -x_{k-n}, u_k, u_{k-1}, \ldots, u_{k-n}]$$

$$\theta' = [a_1, \ldots, a_n, b_0, \ldots, b_n].$$

A special case of the ARMA model above is an MA (moving average system), where $a_1, \ldots, a_n$ and $x(t-1), \ldots, x(t-n)$ disappear in the parameter and regressor, respectively.

The prior information on $\theta$ will be a bounded set $\Omega_1$, which is provided by prior expert knowledge. For example, suppose $$G(s) = \frac{1}{1 + T_s}.$$

Figure 27:
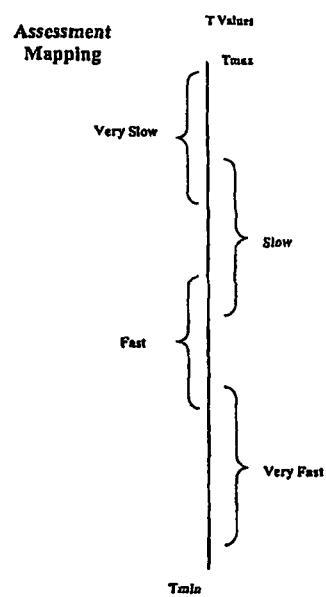
FIG. 27 is a representation of typical assessment mappings.

The model parameter T has a clear physical meaning of response speed and allows direct inputs from expert knowledge. For instance, a patient with fast drug response will have a small T. A linguistic assessment "fast response" can be translated by a pre-designed assessment mapping to a bounded set $[\underline{T}, \overline{T}]$. This information will then be mapped to a bounded set on $\theta$ after discretization. Typical assessment mappings look like the intervals in FIG. 27. This set will serve as prior information for the learning algorithm to be described in the next subsection.

The nonlinear function $f$ can also be parameterized. Usually, polynomials are used. However, polynomials of the form $x^{m-1} + c_{m-2} x^{m-2} + \ldots + c_1 x + c_0$ is not convenient for incorporating expert knowledge. In many medical applications, $f$ represents steady-state sensitivity: The impact of the input (drug amount) on the outcome. A physician's knowledge is often expressed by an approximate relationship between the input and outcome: Given typical input amounts $x_1, \ldots, x_m$, the approximate ranges of the predicted outcomes $[\underline{y}_1, \overline{y}_1], \ldots, [\underline{y}_m, \overline{y}_m]$. To accommodate this knowledge, we replace $1, x, \ldots, x^{m-1}$ by a collection of appropriate functions $\Phi_i(x)$ and introduce the following parameterization for $f$. Suppose that the prior information on $f$ is given by m distinct mappings: $x_i \to [\underline{y}_i, \overline{y}_i]$, $i=1, \ldots, m$ as shown in FIG. 2. We parameterize $f$ by $$y = f(x) = \sum_{i=1}^{m} C_i \Phi_i(x) \quad (1)$$

where $\Phi_i(x)$ is the mth order polynomial $$\Phi_i(x) = \frac{\prod_{j=1, j \neq i}^{m} (x - x_j)}{\prod_{j=1, j \neq i}^{m} (x_i - x_j)}.$$

$\Phi_i(x)$ satisfies $\Phi_i(x_j) = 0$, $j \neq i$; $\Phi_i(x_i) = 1$. In other words, $\Phi_i(x)$ are indicator functions on the set points $\{x_i, \ldots, x_m\}$. The unknown parameters will be denoted by $\ominus = [C_1, \ldots, C_m]'$. Consequently, the prior expert information becomes precisely the prior interval information on the parameters: $C_i \in [\underline{y}_i, \overline{y}_i]$, $i=1, \ldots, m$.

Figure 28:
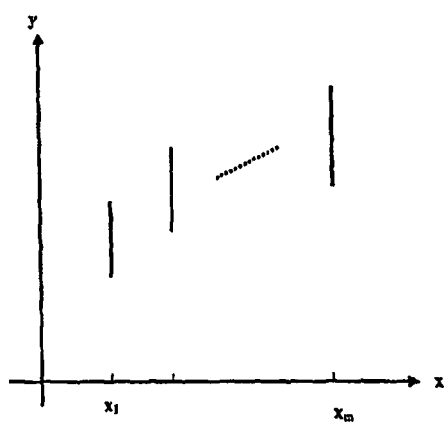
FIG. 28 is a representation of expert knowledge of drug impact on the outcome.
Figure 29:
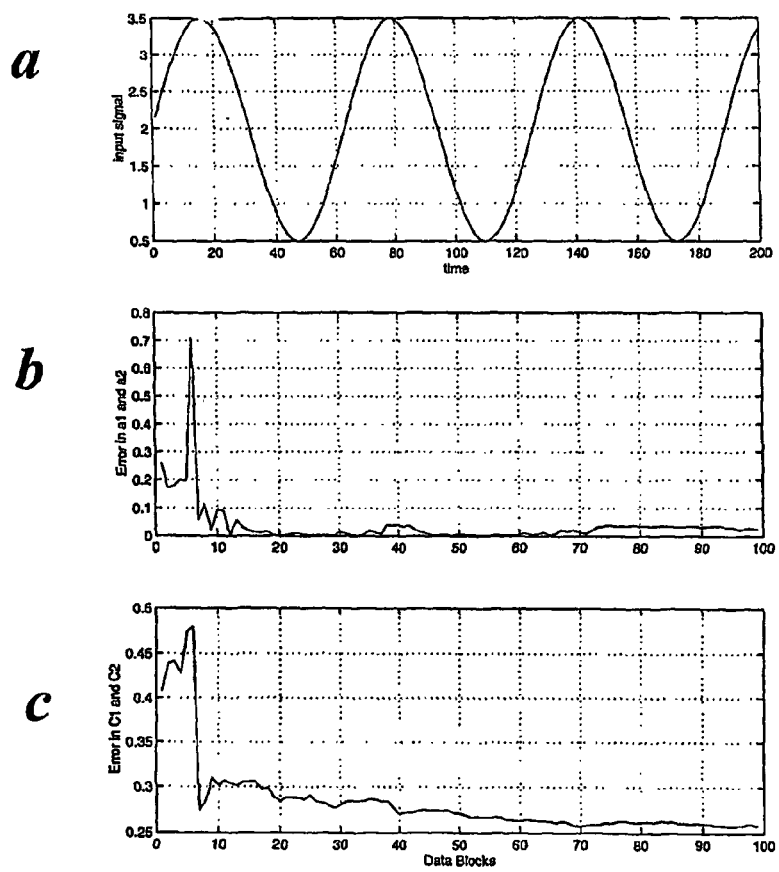
FIGS. 29a to 29c illustrate a two-step recursive estimation.

The expert knowledge will serve as the prior information on the unknown parameters $\theta$ and $\ominus$. It will be generically expressed as $\theta \in \Omega_1$ and $\ominus \in \Omega_2$. Here, $\Omega_1$ and $\Omega_2$ are bounded sets. In many applications, they are simply polyhedres. (See, FIG. 28)

Basic Setup for Real-Time Learning Algorithms

We propose a class of estimation algorithms, which are recursive and can be thought of as a relaxation procedure that uses most recently acquired information. The algorithms are a new twist of the least squares identification algorithms used in a wide variety of applications. Its essence is to use real-time data on the input $\{u_k\}$ and output $\{y_k\}$ as soon as they become available. One of the distinct features of our algorithms is: The identification task is accomplished in two steps. The first step requires mapping the sequenece of outputs back to get a sequence of "intermediate" output, which is used for estimating $\theta$. Then the second step takes care of the estimation of $\ominus$. These estimates are obtained recursively and hence are suitable for on-line computing. The expert prior knowledge is used as constraints in the algorithms. The problem can be stated as follows: Let $\hat{\theta}_k$ and $\hat{\ominus}_k$ denote the estimates of the model parameters at the kth step.[1] We proceed to design an identification algorithm for $\hat{\theta}_k$ and $\hat{\ominus}_k$, based on the prior information $\Omega_1$, $\Omega_2$, and past and present observations on u and y, such that a least squares type cost function is minimized. The following issues are of importance in designing the identification algorithms.

[1] The actual time interval between the kth and the (k+1)st steps depends on the sampling interval of the system.

1. Real-Time Computational Efficiency: During real-time implementation, the data size N becomes larger and larger. Consequently, the computational burden of finding estimates can potentially become overwhelming when N is large. As a result, recursive algorithms which employ newly acquired data $u_k$ and $y_k$ to update the estimate from $\hat{\theta}_k$ and $\hat{\ominus}_k$ to $\hat{\theta}_{k+1}$ and $\hat{\ominus}_{k+1}$, are much more preferrable than their off-line counter part.
2. Nonlinearity: Due to the nonlinear model structure, the numerical solution may be difficult to obtain. Hence, it is desirable to find an approximate optimization problem that is convex or linear.
3. Convergence: We need to establish convergence properties of the designed identification algorithms.

We update the estimates of $\theta$ and $\ominus$ alternately and use the most recently information as soon as they become available. To do, we construct iterative procedures so that the estimates of $\theta$ and $\ominus$ are computed iteratively one followed by the other. To be more specific, we introduce the two-step iterative identification setup below. The more specific algorithms will be given later.

Two-step Procedure. Given the bounded sets $\Omega_1$ and $\Omega_2$, which are given by use of the expert knowledge, and performance indices $e_1(\theta)$ and $e_2(\ominus)$, we start at k=0 with $\hat{\theta}_0$ and $\hat{\ominus}_0$ being interior of $\Omega_1$ and $\Omega_2$, respectively.

Step 1: At time k, suppose that the estimates $\hat{\theta}_k$ and $\hat{\ominus}_k$ have been computed. To construct the next estiamtes, the essence of the least squares approach normally reques a cost function involves the the difference of observations and "weighted" regression be minimized. However, the output, or measurement, or observation $x_k$ is not available. One remedy is to map the available $\hat{\ominus}_k$ back and obtain the "intermediate" output $\hat{x}_k$ using the estimated nonlinear sensitivity function with parameter $\hat{\ominus}_k$. Then use $u_k$ and $\hat{x}_k$ to obtain update $\hat{\theta}_{k+1}$.

The update algorithm is a projected identification recursive scheme
1. $\theta^* = \arg \min_\theta e_1(\theta)$ subject to the constraint $\theta^* \in \Omega_1$. Denote the estimate at the kth step without constraint by $\check{\theta}_k$ and the constraint estimate by $\hat{\theta}_k$. At time k+1, 2. If $\check{\theta}_{k+1} \in \Omega_1$, then $\hat{\theta}_{k+1} = \check{\theta}_{k+1}$.
3. If $\check{\theta}_{k+1} \notin \Omega_1$, then $\hat{\theta}_{k+1}$ is the projection of $\check{\theta}_{k+1}$ onto $\Omega_1$, namely the closest element of $\Omega_1$ to $\check{\theta}_{k+1}$.

Step 2: Now since $\hat{\theta}_{k+1}$ has obtained, we use $u_k$ and $y_k$ to update $\hat{\ominus}_{k+1}$ from $\hat{\ominus}_k$. This is accomplished by minimize another cost function $e_2(\ominus)$ again in the mean sqaures sense.

The update algorithm is also of the projected least-squares identification:

1. $\ominus^* = \arg\min_\ominus e_2(\ominus)$ subject to the constraint $\ominus^* \in \Omega_2$. Denote the unconstrained and the constrained estimates at the (k+1)st step by $\check{\ominus}_{k+1}$ and $\hat{\ominus}_{2k+1}$, respectively.
2. If $\check{\ominus}_{k+1} \in \Omega_2$, then $\hat{\ominus}_{k+1} = \check{\ominus}_{k+1}$.
3. If $\check{\ominus}_{k+1} \notin \Omega_2$, then $\hat{\ominus}_{k+1}$ is the projection of $\check{\ominus}_{k+1}$ onto $\Omega_2$, namely the closest element of $\Omega_2$ to $\check{\ominus}_{k+1}$.

Recursive Algorithms

Least Squares Algorithms

Following the discussion in the previous section, we develop the two-step procedure here. Note that the statistics of $(x_k, \phi_k)$ and $(y_k, \Phi_k)$ may not be known, but their measurements are available.

To begin, we first construct the unconstrained algorithms and obtain its constrained counter part for $\hat{\theta}_k$ and then write the corresponding part for $\hat{\ominus}_k$. In what follows, to signifty the dependence of the cost function on k, we write it as $e_{1,k}(\theta)$.

Consider the problem of minimizing $$e_{1,k}(\theta) = \frac{1}{k}\sum_{i=0}^{k-1}(\hat{x}_i - \theta'\phi_i)^2, \quad (2)$$

where $\hat{x}_k$ are obtained by a back mapping technique via $\ominus_k$. Suppose that the matrix $$\Psi_k = \sum_{i=0}^{k-1}\phi_i\phi_i'$$

is invertible with probability one for k large enough. Then, the minimizing $\theta$ is given by $$\hat{\theta}_k = \Psi_k^{-1}\sum_{i=0}^{k-1}\hat{x}_i\phi_i. \quad (3)$$

Equation (3) can be put into a recursive form by expanding $$\hat{\theta}_{k+1} = \Psi_{k+1}^{-1}\left[\sum_{i=0}^{k-1}\hat{x}_i\phi_i + \hat{x}_k\phi_k\right],$$

to get see [9, pp. 18-20])

$$\hat{\theta}_{k+1} = \hat{\theta}_k + \Psi_{k+1}^{-1}\phi_k[\hat{x}_k - \phi'_k\hat{\theta}_k]. \quad (4)$$

Since a matrix is involved, the computation can be time consuming. To avoid the onerous task, by using the matrix inversion lemma [9, pp. 18-20], we can rewrite the procedure recursively as $$\Psi_{k+1}^{-1} = \Psi_k^{-1} - \frac{\Psi_k^{-1}\phi_k\phi'_k\Psi_k^{-1}}{1+\phi'_k\Psi_k^{-1}\phi_k}, \quad (5)$$

$$\hat{\theta}_{k+1} = \hat{\theta}_k + \frac{\Psi_k^{-1}}{1+\theta'_k\Psi_k^{-1}\phi_k}\phi_k[\hat{x}_k - \phi'_k\hat{\theta}_k].$$

These are known as the recursive least squares formulas.

To further simplify the procedure, taking a first-order (in $\Psi_k^{-1}$) expansion in (4) and (5) yields a linearized least squares approximation $$\hat{\theta}_{k-1} = \hat{\theta}_k + \Psi_k^{-1}\phi_k\hat{\theta}_k + \Psi_k^{-1}\phi_k[\hat{x}_k - \phi'_k\hat{\theta}_k],$$

$$\Psi_{k+1}^{-1} = [I - \Psi_k^{-1}\phi_k\phi'_k]\Psi_k^{-k}. \quad (6)$$

The convergence of the sequences in (5) is assured by any conditions that assure the convergence of the least squares estimator.

Similarly, using the cost function $$e_{2,k}(\Theta) = \frac{1}{k}\sum_{i=0}^{k-1}(y_i - \Theta'\Phi_i)^2, \quad (7)$$

and assuming that $$\Xi_k = \frac{1}{k}\sum_{i=0}^{k-1}\Phi_i\Phi'_i$$

is invertible, we arrive at the recursive least squares procedure for estimating $\ominus^*$ $$\Xi_{k+1}^{-1} = \Xi_k^{-1} - \frac{\Xi_k^{-1}\Phi_k\Phi'_k\Xi_k^{-1}}{1+\Phi'_k\Xi_k^{-1}\Phi_k}, \quad (8)$$

$$\hat{\Theta}_{k+1} = \hat{\Theta}_k + \frac{\Xi_k^{-1}}{1+\Phi'_k\Xi_k^{-1}\Phi_k}\Phi_k[y_k - \Phi'_k\hat{\Theta}_k],$$

and the linearized least squares approximation $$\hat{\ominus}_{k+1} = \ominus_k + \Xi_k^{-1}\Phi_k\hat{\ominus}_k + \Xi_k^{-1}\Phi_k[y_k - \Phi'_k\hat{\ominus}_k],$$

$$\Xi_{k+1}^{-1} = [I - \Xi_k^{-1}\Phi_k\Phi'_k]\Xi_k^{-1}. \quad (9)$$

Adaptive Filtering-Type Procedure

Replacing the matrix gain $\Psi_k$ by a scalar sequence of step sizes leads to further simplification of (6). In fact, we obtain the following recursive algorithm $$\hat{\theta}_{k+1} = \hat{\theta}_k + \epsilon_k\phi_k[\hat{x}_k - \phi'_k\hat{\theta}_k], \quad (10)$$

where $\epsilon_k$ is a sequence of real numbers satisfying $$\varepsilon_k \geq 0, \varepsilon_k \to 0 \text{ as } k \to \infty, \text{ and } \sum_k \varepsilon_k = \infty. \quad (11)$$

Algorithm (10) is a stochastic approximation type procedure, and belongs to the family of adaptive filtering algorithms; see [6] for an updated account on stochastic approximation algorithms. Commonly used step size sequences include $\epsilon_k = O(1/$ k), $\epsilon_k=O(1/k^\gamma)$ for some $0<\gamma<1$, among others. Likewise, for $\hat{\Theta}$, we construct the algorithm as $$\hat{\Theta}_{k+1}=\hat{\Theta}_k+\epsilon_k\Phi_k[y_k-\Phi'_k\hat{\Theta}_k], \qquad (12)$$

where we choose the same sequence $\{\epsilon_k\}$ as in (11).

Constrained Algorithms

For the constrained algorithms, we use projection operators $\Pi_1$ and $\Pi_2$ to denote the projections onto $\Omega_1$ and $\Omega_2$, respectively. Recall that $\Omega_1=\{\theta: \underline{\theta}_i \leq \theta^i \leq \overline{\theta}_i, i=1, \ldots, 2n+1\}$ and $\Omega_2=\{\Theta:\underline{\Theta}_i \leq \Theta^i \leq \overline{\Theta}_i, i=1, \ldots, m\}$, respectively. That is, we let the ith component of the estimates $\hat{\theta}$ and $\hat{\Theta}$ be confined to the interval $[\underline{\theta}_i, \overline{\theta}_i]$ and $[\underline{\Theta}_i, \overline{\Theta}_i]$, respectively. Similar to the previous cases, the constrained algorithms can be written as $$\hat{\theta}_{k+1}=\Pi_1[\hat{\theta}_k+\epsilon_k[\tilde{x}_k-\Phi'_k\hat{\theta}_k]],$$

$$\hat{\Theta}_{k+1}=\Pi_2[\hat{\Theta}_k+\epsilon_k[y_k-\Phi'_k\hat{\Theta}_k]]. \qquad (13)$$

Variants

Comparing the least squares algorithms with that of the adaptive filtering algorithms, their differences are seen in the step size sequences involved. Consequently, the adaptive filtering type algorithms have the advantage over that of the least squares algorithm since one need not warry about matrix manipulations for the step size sequences. As far as the computational complexity is concerned, the real-valued step sizes are more preferrable. Nevertheless, it is also clear that the least squares algorithms use more information compared to the adaptive filtering procedures owing to the use of the matrix gain sequence. Therefore, it is expected that the least squares algorithm provided better performance owing to the use of matrix gain. One question is almost immediate. Can we construct an algorithm that has the advantage as that of the adaptive filtering procedures with reduced complexity, in the mean time, still provides good performance? In other words, we wish to construct algorithms that have advantages of both adaptive filtering type and that of the basic least squares procedure. The ideas of averaging becomes a favorable alternative, which was initially considered in [12, 14] and subsequently treated in [5, 20] for much more general noise processes; see also [1, 15, 20] for averaging applied to both iterates and observations. In what follows, we present two of such averaging procedures. Both of them give rise to asymptotically efficient schemes. We will show that the averaging algorithms so constructed yield asmptotic optimality. By asymptotic optimality, we mean that not only is the scaling factor the best one, but also the limit covariance is the smallest possible.

Suppose that $\hat{\theta}_k \to \theta^*$ the true parameter with probability one. For the rate of convergence, we examine the sequence $k^\alpha(\hat{\theta}_k-\theta^*)$. We try to find such real number $\alpha$ that the above rescaled sequence converges to a nontrivial limit in the sense of convergence in distribution. The scaling factor $k^\alpha$ together with the asymptotic covariance then gives us the desired convergence rate.

Constant-Step-Size Algorithms

In lieu of decreasing step-size sequences used in (13), we may consider algorithms with constant-step size. In fact, in various signal processing applications, one normally uses a constant step size rather than a sequence of decreasing step sizes. The rationale is that the use of a constant gain normally enables one to track slight variation of the parameter. In reality, the parameters involved in patient responses to anesthetic drug infusion are not fixed constants, but rather time varying. Thus, the tracking ability is important. For our problem, suggest the following constant-step algorithms with constraints.

$$\hat{\theta}_{k+1}=\Pi_1[\hat{\theta}_k+\epsilon[\tilde{x}_k-\Phi'_k\hat{\theta}_k]],$$

$$\hat{\Theta}_{k+1}=\Pi_2[\hat{\Theta}_k+\epsilon[y_k-\Phi'_k\hat{\Theta}_k]]. \qquad (14)$$

Note that in (14), $\hat{\theta}_k$ and $\hat{\Theta}_{k+1}$ in fact depend on $\epsilon$ and should have been written as $\hat{\theta}_k^\epsilon$ and $\hat{\Theta}_{k+1}^\epsilon$, respectively. For notational simplicity, we have suppressed the $\epsilon$-dependence. To be able to get meaningful asymptotic results for algorithm (14), we need to let $\epsilon \to 0$. In the actual computation, one uses a small fixed constant $\epsilon$.

Iterate Averaging

The idea behind this scheme is: First one obtains a rough estimate via the use of larger than $O(1/k)$ step sizes. Then one takes an averaging of the iterates. One of the particular attractive features of the algorithm is that the use of large step size creats oscilations and force the iterates moving towards the target faster than the use of smaller step sizes. In addition, although the averaging is essentially off-line, it can be executed recursively. We shall work with the constrained algorithm since we have the expert knowledge at our hands. In what follows we use $\epsilon_k$ that goes to 0 slower than $O(1/k)$, i.e., $(1/k)/\epsilon_k \to 0$ as $k \to \infty$. Construct $$\begin{cases} \hat{\theta}_{k+1} = \prod_1 [\hat{\theta}_k + \varepsilon_k[\hat{x}_k - \phi'_k\hat{\theta}_k]], \\ \overline{\theta}_{k+1} = \overline{\theta}_k - \frac{1}{k+1}\overline{\theta}_k + \frac{1}{k+1}\hat{\theta}_{k+1} \end{cases} \qquad (15)$$

for estimating $\theta^*$ and $$\begin{cases} \hat{\Theta}_{k+1} = \prod_2 [\hat{\Theta}_k + \varepsilon_k[y_k - \Phi'_k\hat{\Theta}_k]], \\ \overline{\Theta}_{k+1} = \overline{\Theta}_k - \frac{1}{k+1}\overline{\Theta}_k + \frac{1}{k+1}\hat{\Theta}_{k+1} \end{cases} \qquad (16)$$

for estimating $\Theta^*$.

Averaging in Both Iterates and Observations

An alternative of the iterate averaging calls for the use of averaging in both iterates and outputs (observations)

$$\begin{cases} \hat{\theta}_{k+1} = \prod_1 [\theta_k + \varepsilon_k k \overline{X}_k], \\ \overline{X}_k = \frac{1}{k}\sum_{i=0}^{k} \phi_i[\hat{x}_i - \phi'_i\hat{\theta}_i], \\ \overline{\theta}_{k+1} = \overline{\theta}_k - \frac{1}{k+1}\overline{\theta}_k + \frac{1}{k+1}\hat{\theta}_{k+1}, \end{cases} \qquad (17)$$

and similarly, $$\begin{cases} \hat{\Theta}_{k+1} = \prod_2 [\Theta_k + \varepsilon_k k \overline{Y}_k], \\ \overline{Y}_k = \frac{1}{k}\sum_{i=0}^{k-1} \Phi_i[y_i - \Phi'_i\hat{\Theta}_i], \\ \overline{\Theta}_{k+1} = \overline{\Theta}_k - \frac{1}{k+1}\overline{\Theta}_k + \frac{1}{k+1}\hat{\Theta}_{k+1}. \end{cases} \qquad (18)$$

Convergence and Rates of Convergence

In this section, we study asymptotic properties including convergence and rates of convergence of the recursive algorithms proposed in the last section. In fact, our attention will be devoted to the constrained algorithms using iterate averaging and/or averaging of both iterates and observations. Sufficient conditions will be provided, and existing results will be used whenever possible. The main ideas of development will be presented although verbatim proofs will be omitted. To proceed, we need the following assumptions.

(A1) The sequences $\{(\hat{x}_k, \phi_k)\}$ and $\{(y_k, \Phi_k)\}$ are stationary martingale difference processes. That is, with probability one (w.p1), $$E[(\hat{x}_k,\phi_k)|(\hat{x}_{k-1},\phi_{k-1}),\ldots,(\hat{x}_0,\phi_0)]=0, \text{ and}$$

$$E[(y_k,\Phi_k)|(y_{k-1},\Phi_{k-1}),\ldots,(y_0,\Phi_0)]=0.$$

(A2) The following moment conditions hold.

$$E\phi_k\phi'_k=A_\phi, E\Phi_k\Phi'_k=A_\Phi, E\phi_k\hat{x}_k=B_\phi, E\Phi_k y_k=B_\Phi,$$

where $A_\phi$ and $A_\Phi$ are symmetric and positive definite. Moreover, $$E[|\hat{x}_k|^2+|\phi_k|^2+|y_k|^2+|\Phi_k|^2]<\infty.$$

Remark 1. A special case of the martingale assumption deals with sequences of independent and identically distributed random vairables. However, more generally a martingale difference sequence is not necessarily independent but is uncorrelated. We note that allowing correlated signals is important since in the anethesia infusion problem we consider due to the operating conditionss, the influence of various noise sources in the enviroment, the signals generally will be correlated. The uncorrelated condition is only a crude approximation. We choose such a condition since it is easier to understand and more accessible to wider audience. It seems to be more instructive to present the main ideas than searching for the weakest conditions.

More general correlated noise such as $\phi$-mixing processes, which in fact allows diminishing correlations between the remote past and distant future; interested reader is referred to [5, 20] and the references therein. However, for ease of presentation, we confine our attention to the uncorrelated signals. To make the paper more accessible and appealing to wider range of audience, the assumptions given are much stronger than necessary. Our hope is that we will be able to get the main ideas accrossed without undue much of the technical difficulties.

Convergence

In what follows, we illustrate how the algorithms can be analyzed by using (17). The main ideas are outlined, but the verbatim proofs will be omitted. To analyze the algorithm, note that the first equation in (17) can be rewritten as $$\hat{\theta}_{k+1}=\hat{\theta}_k+\epsilon_k\phi_k[\hat{x}_k-\phi'_k\hat{\theta}_k]+\epsilon_k R_{\phi,k},$$

where $$\epsilon_k R_{\phi,k}=\hat{\theta}_{k+1}-\hat{\theta}_k-\epsilon_k\phi_k[\hat{x}_k-\phi'_k\hat{\theta}_k]$$

is the vector having shortest Euclidean length needed to bring $\epsilon_k\phi_k[\hat{x}_k-\phi'_k\hat{\theta}_k]$ back to the constraint set $\Omega_1$.

To prove the convergence of the recursive algorithms, in lieu of considering the discrete resurvie directly, we take a contiuous-time interpolation and work on appropriate function spaces. To be more specific, define $$t_0=0, \text{ and } t_k=\sum_{i=0}^{k-1}\varepsilon_i,$$

$$m(t)=\begin{cases} k, & 0\le t_k\le t<t_{k+1}, \\ 0, & t<0, \end{cases}$$

and $$\theta^0(t)=\hat{\theta}_k \text{ for } t\in[t_k,t_{k+1}),$$

$$\theta^k(t)=\theta^0(t+t_k).$$

That is $\theta^0$ (t) is the piecewise constant interpolation of $\hat{\theta}_k$ and $\theta^k(t)$ is a sequence obtained by shifting $\theta^0$ (t) sequence that enables us to bring the "tail" of the sequence to the foreground. For a more detailed account on the interpolations, see [6, pp. 90-92]. Similarly, define $$R_\phi^0(t)=0 \text{ for } t\le 0, \quad R_\phi^0(t)=\sum_{i=1}^{m(t)-1}\varepsilon_i R_{\phi,i}, \text{ for } t\ge 0,$$

$$R_\phi^k(t)=R_\phi^0(t+t_k)-R_\phi^0(t_k), \text{ for } t\ge 0$$

and $$R_\phi^k(t)=-\sum_{i=m(t+t_k)}^{k-1}\varepsilon_i R_{\phi,i}, \text{ for } t<0.$$

To proceed, define a set $C(\theta)$ as follows. For $\theta\in\Omega_1^o$, the interior of $\Omega_1$, $C(\theta)$ contains only the zero element. For $\theta\in\partial\Omega_1$, the boundary of $\Omega_1$, $C(\theta)$ is the convex cone generated by the outer normal at $\theta$ at which $\theta$ lies. Owing to the projection used, it is easily seen that $\{\hat{\theta}_k\}$ is bounded uniformly, and as a result $\{\theta^k(\bullet)\}$ is a sequence of uniformly bounded function. Moreover, it can be shown that $\{\theta^k(\bullet),R_\phi^k(\bullet)\}$ is equicontinuous in the extended sense ([6, p. 72]). By virtue of an extended version of the Ascoli-Arzelá theorem, there is a subsequence that converges to some continous limit uniformly on each bounded time interval. Thus, we arrive the following result; the detailed proof may be found in [6, Chapter 5].

Lemma 1. Under conditions (A1) and (A2), $\{\theta^k(\bullet),R_\phi^k(\bullet)\}$ is uniformly bounded and equicontinuous in the extended sense. There exists a convergent subsequence with limit $(\theta(\bullet),R_\phi(\bullet))$ satisfying the projected ordinary differential equation $$\dot{\theta}=B_\phi-A_\phi\theta+\tau_\phi, \tau_\phi(t)\in -C(\theta(t)), \qquad (19)$$

where $R_\phi(t)=\int_0^t \tau_\phi(s)ds$. Likewise, $\{\Theta^k(\bullet),R_\Phi^k(\bullet)\}$ has convergent subsequence with limit $(\Theta(\bullet),R_\phi(\bullet))$ satisfying the projected ODE $$\dot{\Theta}=B_\Phi-A_\Phi\Theta+\tau_\Phi, \tau_\Phi(t)\in -C(\Theta(t)), \qquad (20)$$

where $R_\Phi(t)=\int_0^t \tau_\Phi(s) ds$.

Remark 2. The significance of the (19) is that its stationary points are precisely the values of the parameter we are looking for. In view of the expression (19), $\tau_\phi(\bullet)$ is the term needed to keep $\theta(\bullet)$ in $\Omega_l$. Interested reader is referred to [6, Section 4.3] for futher details. The significance of the $\tau_\phi(\bullet)$ for the drug infusion process is that the expert knowledge allows us to keep the dynamics within a bounded region.

Theorem 3. In addition to the conditions of Lemma 1, suppose that there is a unique stationary point $\theta^*$ to the ODE (19). Then $\hat{\theta}_k$ converges to $\theta^*$ w.p.1. Moreover, $\overline{\theta}_k\to\theta^*$ w.p.1. Similarly, suppose that there is a unique stationary point $\Theta^*$ to the ODE (20). Then $\hat{\Theta}_k$ and $\overline{\Theta}_k$ converge to $\Theta^*$ w.p.1.

The proof of convergence of $\{\hat{\theta}_k\}$ follows from that of the argument in [6, Theorem 5.1], whereas the convergence of $\overline{\theta}_k$ is a consequence of a familiar fact in analysis (namely, if a sequence converges to a limit then so does its arithmetic average).

The uniqueness assumption on the stationary point is guranteed by the choosing the projection bounds to be large enough such that $\underline{\theta}_i<0$ and $\overline{\theta}_i>0$, $i\leq 2n+1$. An argument using a form of the Kuhn-Tucker points and the ideas of active constraints to verify the assertion is in [6, Section 9.4]. When $\theta \in \Omega_1^0$, $\tau_\phi=0$. Note that interior to $\Omega_l$, the dynamics of the trajectories are determined by the ODE $\dot{\theta}=B_\phi-A_\phi\theta$. This is a linear ODE and hence has a unique solutino for each initial condition. The stationary point of this ODE is precisely $\theta^*=A_\phi^{-1}B_\phi$. In the actual calculation using the recursive algorithm, if the iterates repeatedly hover the bounding surface, we would increase the size of the projection region. Similar discussion applies to the recursive estimates $\{\hat{\Theta}_k\}$.

Rate of Convergence

For the study of rate of convergence, we concentrate on both iterate averaing algorithms and algorithms with averaging in both iterates and observations in what follows.

Let us begin with (13), under the assumptions of Theorem 3, $\hat{\theta}_k \to \theta^*$ w.p.1 and $\theta^* \in \Omega_1^0$. Thus effectively, the truncation or projection can be dropped in the rate of convergence analysis. Define $$\xi_k=\Phi_k(\hat{x}_k-\Phi'_k\theta^*), \tilde{\theta}_k-\theta^*,$$

$$\eta_k=\Phi_k(y_k-\Phi'_k\Theta^*), \tilde{\Theta}_k=\overline{\Theta}_k-\Theta^*.$$

Dropping the projection term and setting $$D_{k|j} = \begin{cases} \prod_{l=j+1}^{k}(I-\varepsilon_l A_\phi), & \text{if } j<k, \\ I, & \text{if } j=k, \end{cases}$$

we have $$\tilde{\theta}_{k+1} = (I-\varepsilon_k A_\phi)\tilde{\theta}_k + \varepsilon_k \xi_k + \varepsilon_k[A_\phi-\phi_k\phi'_k]\tilde{\theta}_k \quad (21)$$

$$= D_{k|0}\tilde{\theta}_0 + \sum_{j=0}^{k}\varepsilon_j D_{k|j}\xi_j + \sum_{j=0}^{k}\varepsilon_j D_{k|j}[A_\phi-\phi_j\phi'_j]\tilde{\theta}_j.$$

Using (21), we will be able to obtain a distributional limit. The statement is in the following theorem. Its proof can be obtained as in [6, Chapter 10]. In fact, in the reference, we dealt with stochastic processes aspect of the problem by taking continuous-time interpolations and worked with interpolated processes, and proved a limit stochastic differential equation holding for the centered and rescaled sequence.

Theorem 4 Under the conditions of Theorem 3, for the algorithm given in (13), $(\hat{\theta}_k-\theta^*)/\sqrt{\varepsilon_k}$ converges in distribution to $N(0,\Sigma_\phi)$ a normal random variable with mean 0 and covriance $\Sigma_\phi=E\xi_1\xi'_1$, and $(\hat{\Theta}_k-\Theta^*)/\sqrt{\varepsilon_k}$ converges in distribution to $N(0,\Sigma_\Phi)$, where $\Sigma_\Phi=E\eta_1\eta'_1$.

The scaling factor $1/\sqrt{\varepsilon_k}$ together with the asymptotic covariances $\Sigma_\phi$ and $\Sigma_\Phi$ gives thedesired rates of convergence. We next demonstrate that iterate averaging and averaging in both iterates and observations lead to improved convergence speed. To fix the idea, we choose $\varepsilon_k=(1/(k+1)^\gamma)$ with $1/2<\gamma<1$. Define $$\overline{w}_k = \frac{1}{\sqrt{k}}\sum_{j=0}^{k}\tilde{\theta}_j,$$

$$\overline{W}_k = \frac{1}{\sqrt{k}}\sum_{j=0}^{k}\tilde{\Theta}_j.$$

Using (21), we can show that $$\overline{w}_k = -\frac{A_\phi}{\sqrt{k}}\sum_{j=0}^{k}\xi_j + o(1),$$

where $o(1) \to 0$ in probability as $k \to \infty$. Similar result holds for $\overline{W}_k$. We finally arrive at:

Theorem 5. Under the conditions of Theorem 4, for the iterative averaging algorithms, $\sqrt{k}(\overline{\theta}_k-\theta^*)$ converges in distribution to $N(0, A_\phi^{-1}\Sigma_\phi A_\phi^{-1})$ and $\sqrt{k}(\overline{\Theta}_k-\Theta^*)$ converges in distribution to $N(0, A_\Phi^{-1}\Sigma_\Phi A_\Phi^{-1})$. The conclusions continue to hold for algorithms (17) and (18).

Discussion on Asymptotic Optimality

Consider $\hat{\theta}_k$ given by (13). In view of Theorem 4, if we take $\varepsilon_k=O(1/k^{\gamma, \text{with}}\ 0<\gamma\leq 1$. Apparenetly, the best possible scaling factor is by using $\varepsilon_k=O(1/k)$. However, now the algorithm is stochastic. The convergence rate is determined not only by the scaling factor but also by its variations (variances). To examine further, take $\varepsilon_k=\Gamma/k$, where $\Gamma$ is a matrix. According to Theorem 4, $\sqrt{k}(\hat{\theta}_k-\theta^*)$ is asymptotically normal and its asymptotic covariance $\tilde{\Sigma}_\phi$ in fact depends on $\Gamma$, i.e., $\tilde{\Sigma}_\phi=\tilde{\Sigma}_\phi(\Gamma)$. Minimizing the covariance or its trace with respect to $\Gamma$, we obtain that the "smallest" covariance is given by $A_\phi^{-1}\Sigma_\phi(A_\phi^{-1})'$. This suggests that one may wish to construct another sequence to estimate $\tilde{\Sigma}_\phi$ and use that in algorithm (13). Nevertheless, a moment of reflection shows that such an idea is not feasible since it is computational intersive. The results in Theorem 5 show that by using averaging approaches, we obtain asymptotically optimal performance of the algorithms without carrying out the tedious estimation procedures. In addition, the use of large step size (larger than $O(1/k)$) provides better transient behavior.

Simulation and Illustration

Utility of the recursive algorithms presented in the above subsections will be illustrated here by a numerical example. They will be applied to the anesthesia modeling in the subsequent sections. The example plant is expressed by the following Wiener system $$x(k) = a_1 u(k) + a_2 u(k-1) + w, y(k)$$

$$= 2x(k) + C_1 \frac{x(k)(x(k)-x_2)}{x_2(x_2-x_3)} + C_2 \frac{x(k)*(x(k)-x_3)}{x_3(x_3-x_2)} + v,$$

where the true parameters are $a_1=2$; $a_2=1$; $C_1=4.1$; $C_2=3.5$. The testing points for the expert information on the nonlinear function are $\xi_1=0$; $\xi_1=5$; $\xi\mathbf{3}=10$. For anesthesia applications, we always have $y=0$ when $x=0$. This information is already incorporated in the expression. The nominal function $y=2x$ is known and contained in the expression. Prior information on unknown parameters are given by: range of $a_1=[0,3]$; range of $a_2=[0,2]$; range of $C_1=[2,6]$; range of $C_2=[1,5]$. They will form $\Omega_1$ and $\Omega_2$ by Cartesian products. w and v are i.i.d. uniformly distributed random processes, in the range $[-1.5, 1.5]$.

The two-step structure and the stochastic approximation algorithms are used to identify $\theta=[a_1,a_2]'$ and $\Theta=[C_1,C_2]'$. As expected, the accuracy and convergence of the estimates depend on the input signal (for richness in its probing capability), step sizes, and prior information. Many variations on these conditions are tested: for inputs: the step input, periodic inputs of different periods and typical anesthesia infusion profiles; for step sizes: constant sizes of different values, variable sizes of different initial values and decaying rates; for prior information: different ranges. A typical estimation error trajectory is illustrated in FIG. 3, which has a periodic input and variable step size $\epsilon_k=0.5k^{-0.9}$ for both $\theta$ and $\ominus$ estimators. The resulting estimation: $\hat{\theta}$=[2.04, 1.03]' and $\hat{\ominus}$=[4.21, 2.9951]', much improved accuracy from the prior expert assessment.

Model Development for Patient BIS Responses to Drug Infusion

It is a great challenge to characterize mathematically a patient's response to drug infusion. Due to large deviations in physical conditions, ages, metabolism, pre-existing medical conditions, and surgical procedures, patients demonstrate high nonlinearity and a large variations in their responses to drug infusion. Also, detailed models of clinical subjects on their physiological processes are inherently very complex and not suitable for clinical applications. On the other hand, anesthesiologists have been administering drug infusion successfully with only limited information on patients, such as weights and medical conditions. Control strategies of an experienced anesthesiologist are based intuitively on basic characteristics. such as how sensitive the patient is to a drug infusion. The modeling approach, previously introduced captures this understanding and is briefly summarized below.

Model Structures

The model contains three building blocks, as shown in FIG. 1 The first two blocks represent the patient response to popofol titration and bolus injection, respectively. The third block characterizes the patient response to predictable stimulation such as incision, closing, etc. For concreteness, we will assume that propofol is the anesthesia drug although the model structure is generic and valid for other anesthesia drugs.

Propofol titration is administered by an infusion pump, whose dynamics is represented by a first-order dynamic delay $$\frac{1}{T_i s + 1}$$

where $T_i$ is the time constant of the infusion pump. $T_i$ typically ranges from 0.2 to 2 seconds and is determined from experiment data.

The key component of the model is the patient dynamics, which is defined by three basic elements: (1) Initial time delay $\tau_p$ after drug infusion, represented by a transfer function $e^{-\tau_p s}$; (2) Time constant $T_p$ representing the speed of response, $$\frac{1}{T_p s + 1};$$

(3) A nonlinear static function representing sensitivity of the patient to a drug dosage at steady state, represented by a nonlinear function $f_p$. The meanings of these three components are depicted in FIGS. 2a and 2b.

Two possible model structures for titration are shown in FIG. 3. depending on if the nonlinear function preceeds the linear dynamic system (Hammerstein Model) or follows it (Weiner Model). Both model structures are viable in this application. For simplicity, we shall focus on the Wiener model. The delay time $\tau_p$, time constant $T_p$, and the sensitivity function vary greatly among patients and must be established individually for each patient.

Bolus injection inputs a large amount of drug in a short time interval. The bolus model has a structure similar to the titration model, but with different model parameters, that are correlated to those of the titration model.

One of the most important control tasks in infusion control is to predict the impact of surgical stimulation on the BIS levels. Surgical stimulation is the main cause that induces large fluctuations in anesthetic denth during a surgical procedure. Early prediction of the impact will allow advanced drug adjustment before a feedback signal from the BIS monitor activates control actions. Typical surgical stimulation includes initial surgery preparation, incision, closing, etc. Significant surgical stimulation is predictable in advance and can be roughly characterized by their severity in affecting BIS values. Here we use classification levels from 1 to 5 to represent severity of stimulation: 1 being a minor stimulation and 5 the most significant stimulation. Patient responses to surgical stimulation are represented by the third model block. The block contains also a time delay $\tau_s$ and a transfer function $$\frac{K_s}{T_s s + 1}$$

to reflect its dynamics and a lookup table for its impact on the BIS levels. Since a patient's BIS sensitivity to stimulation depends on hypnosis state, a scaling factor $\alpha$ is introduced, Stimulation Level $\times \alpha$=Scaled Stimulation Level The scaled stimulation is then used to predict the impact on the BIS measurements. Information on an upcoming stimulation will be used as a pre-warning to provide a predictive control so that the impact of the stimulation can be promptly compensated by early tuning of drug infusion.

The BIS monitor measures the EEG signals and performs bi-spectrum statistical analysis. Due to the processing time and data windows required in this procedure, the BIS monitor introduces a pure time delay (from processing time) and a dynamics delay (related to the size of data windows). Its relevant dynamics to control can be represented by a system transfer function $$e^{\tau_b s} \frac{1}{T_b s + 1}$$

cascaded with a nonlinear limiter with lower limit 0 and upper limit 100 (defining the BIS range).

There are many sources of disturbances that will also affect the BIS readings. These include unpredictable stimulation to the patient, other drugs, electrical noises, sensor attachment movements, environment noises, etc. These disturbances are unpredictable and cannot be compensated by early predictive control. Their impact on BIS levels will be minimized by a feedback action.

Model Verification and Development by Clinical Data

To verify the utility of the model structure and develop individual patient models, clinical data are collected, after an approval from the IRB board. One of these data sets is described below to illustrate the process and results.

The anesthesia process was administered manually by an anesthesiologist and lasted about 76 minutes, starting from the initial drug administration and continuing until the last dose of administration. The trajectories of titration and bolus injection, as well as the corresponding BIS values are shown in FIG. 5. Scaled surgical stimulation trajectories are determined by the anesthesiologist and shown in FIG. 6.

Figure 30:
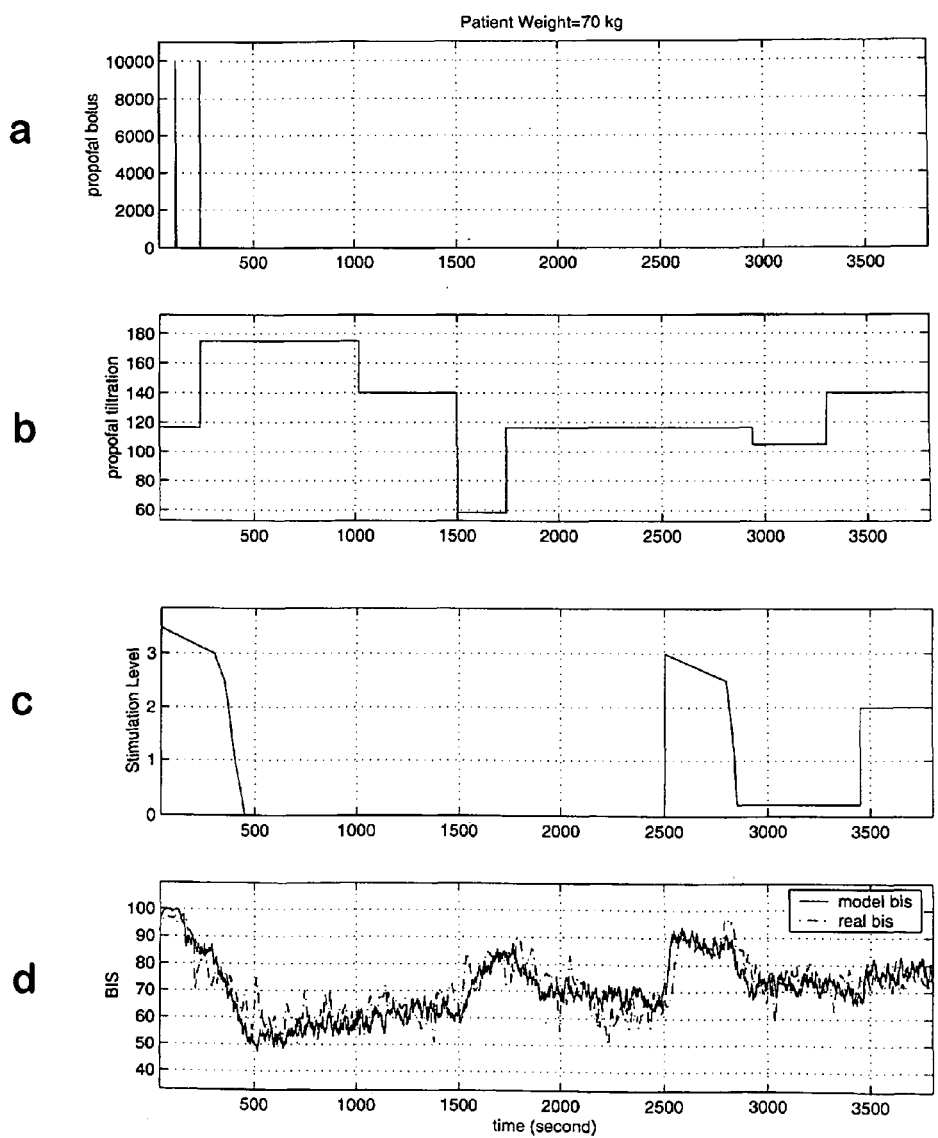
FIGS. 30a to 30d illustrate a patient model response.

The data were then used to determine model parameters and function forms. The Wiener model is used in this case. The actual BIS response is compared to the model response over the entire surgical procedure. Comparison results are shown in FIG. 30. Here, the inputs of titration and bolus are the recorded real-time data. The model output represents the patient response very well. In particular, the model captures the key trends and magnitudes of the BIS variations in the surgical procedure. This indicates that the model structure contains sufficient freedom in representing the main features of the patient response. Also, the impact of surgical stimulation is captured by the model. These features are of essential importance in designing control strategies for computer-aided drug infusion.

Real-Time Identification of the Patient Model

In the previous section, by using an off-line modeling process we have shown that the model structures can represent satisfactorily the patient response to drug infusion. In clinical applications, this model must be developed individually for each patient and modified over the surgical procedure. Consequently, fast real-time modeling becomes inevitable. The main goal of real-time modeling is to obtain the model parameters quickly and accurately.

Employing the identification method and the patient model we will develop a fast identification method for patient models in anesthesia infusion. The algorithm contains two modules: Expert Classification Module (ECM) and Real-Time Learning Module (RTLM). For simplicity, we shall focus on the titration model. The Wiener model entails a linear time-invariant system (time delay and time constant) followed by a memoryless nonlinear function (sensitivity function). Mathematically, this relationship is expressed as $$X(s) = \frac{1}{T_p s + 1} e^{-T_b s} U(s);$$

$$y_k = f_p(x_k)$$

where U(s) is the Laplace transform of the input u (the propofol titration rate). The BIS value is related to y by $$BIS_k = 100 - Sat(y_k)$$

where Sat is the saturation function defined by Sat(y)=y, if $0 \leq y \leq 100$; Sat(y)=0, if y<0; and Sat(y)=100, if y>100. This expression simply represents the fact that the drug infusion will reduce the BIS value from its maximum value 100 (fully awake).

Since the model parameters $T_p$ and $\tau_p$ have clear physical meaning and are compatible with the accessment of an anesthesiologist, this model allows direct inputs from expert knowledge. For instance, a patient with fast drug response will have a smaller $T_p$ and $\tau_p$. It should be emphasized that such a subjective accessment is not accurate and can serve only as initial parameter ranges.

The sensitivity function $f_p$ is a monotone increasing function (the higher the drug infusion rate, the stronger the drug impact), and $f_p(0)=0$. In this application, m=3 is sufficient and typical set points are selected to be $x_1=50$, $x_2=100$, $x_3=150$. To accommodate the condition $f_p(0)=0$, the base functions in (1) is slightly modified to $$y = f_p(x) = C_1 \frac{x}{x_1} \Phi_1(x) + C_2 \frac{x}{x_2} \Phi_2(x) + C_3 \frac{x}{x_3} \Phi_3(x).$$

The coefficients difer significantly from patient to patient. Determination of the coefficients $C_1$, $C_2$, $C_3$, and $\tau_p$ and $T_p$, will be the main task for real-time learning.

The Expert Classification Module

Since control strategies must be decided at the outset of the surgery, one must obtain initial patient characteristics to determine the initial control action. Without real-time data, these parameters must be initiated by expert assessment. The expert knowledge of an anesthesiologist on a patient's drug response pattern is obtained from a patient's medical history and conditions. An anesthesiologist employs the informatioin to give an initial approximate accessment, usually expressed in linguistic terms such as "this is a patient who may be very sensitive to propofol."

The Expert Classification Module (ECM) represents a mapping from the linguistic assessment to initial values $\tau_p$, $T_p$, and $C_1$, $C_2$, $C_3$. Here, we ask an anesthesiologist to assign a relative value between 1 and 10 to represent a patient's resp[onse to drug infusion, where 1 represents the slowest and 10 the fastest. A computerized mapping translates the assessment to a bounded parameter set on $\tau_p$ and $T_p$, as shown in FIG. 10.

For an individual patient, the anesthesiologist provides an initial assessment on drug sensitivity: Given the titration rate $x_i$, the corresponding estimated ranges of BIS values $[\underline{y}_i, \overline{y}_i]$, i=1, 2, 3. This leads to the prior parameter uncertainty set $\Omega_2 = [\underline{y}_1, \overline{y}_1] \otimes [\underline{y}_2, \overline{y}_2] \otimes [\underline{y}_3, \overline{y}_3]$ where X is the Cartisian product.

This framework allows seamless incorporation of expert knowledge into the mathematical model structure even when this knowledge is partial and approximate.

The Real-Time Learning Module

Starting from the initial model uncertainty sets $\Omega_1$ and $\Omega_2$, the Real-Time Learning Module (RTLM) employs real-time data to learn the patient characteristics and to improve model accuracy. Algorithm 1 is employed in this module to identify the parameters recursively.

Verification

The algorithm is evaluated by using the collected clinical data. Under manual control of drug infusion by an anesthesiologist, the popofol titration, bolus injection, surgical stimulation, and the patient response are recorded. The actual samling interval for the BIS trajectory is 5 seconds and the rate change of the drug infusion is timed and recorded manually. For the convenience of data processing, the data are then reformated and resampled (interpolation) to form a synchronized input-output data with sampling interval 1 second.

To illustrate, we shall concentrate on identification of the titration model. To estimate the parameters in the titration block, the data in the interval where the bolus and stimulation impact is minimal are used. A data window of 8 minutes is used in the identification process. The identification proceeds as follows.

First, a grid of potential values of the time delay $T_d$ and the time constant $T_p$ is generated. In this particular application, a grid width of 2 seconds is used for $T_d$ and a grid width of 5 seconds is used for $T_p$, resulting in a grid space G of size $m_d \times m_p$, $(T_d^i, T_p^j)$, i=1, ..., $m_d$, j=1, ..., $m_p$. Due to robustness in feedback and predictive control, this level of precision is sufficient. For each selection of the values from the grids, we estimate the sensitivity function by optimized data fitting (least-squares). Then the fitting errors are compared over the grid space G. The optimal ($T_d^{opt}$, $T_p^{opt}$) is selected that minimizes the fitting error.

Figure 31:
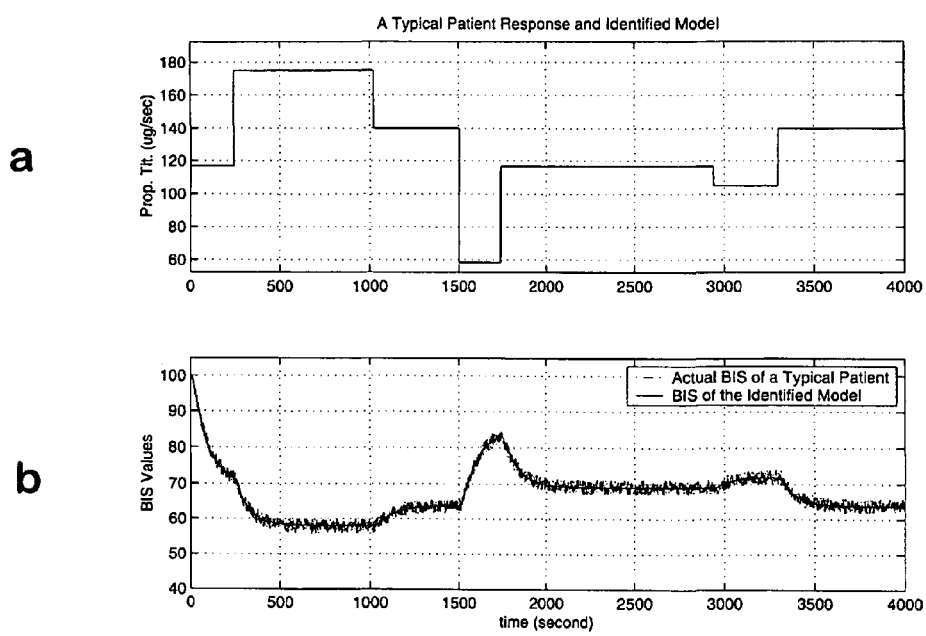
FIGS. 31a and 31b illustrate a real-time identified model.

The actual BIS response is then compared to the model response over the entire surgical procedure. FIG. 31 shows the model BIS trajectory versus the actual BIS data from the patient.

Real-time medical decisions are exemplified by general anesthesia for attaining an adequate anesthetic depth (consciousness level of a patient), analgesia (pain management), sedation control in ICU (intensive care units), fluid resuscitation in trauma cases, circulation control (ventilation and mechanical circulation), etc. In all s these medical decision processes, one of the most critical requirements is to predict the impact of the inputs (drug infusion rates, fluid flow rates, airway pressure and flow rates, etc.) on the outcomes (consciousness levels, pain scores, blood pressures, heart rates, oxygen saturation, etc.). This prediction capability is not necessarily "control-oriented," although its control implication is obvious. It can be used for display, warning, predictive diagnosis, decision analysis, outcome comparison, etc.

The core function of this prediction capability is embedded in establishing, in real-time, a reliable model that relates the (multiple) inputs to the (multiple) outcomes. Apparently, this is a real-time identification problem. This problem offers a great challenge and opportunity for advancing system identification.

The major challenges that must be addressed include:

(1) Reliability and safety are mandatory. Theoretical analysis and limited simulation must be further enhanced by a more comprehensive evaluation process. Eventually reliability must be established statistically via clinical trials.

(2) The characteristics of patient responses demonstrate significant nonlinearity and time variation.

(3) Unlike industry applications, patient responses depend critically on patient medical conditions, surgical procedures, and drug interactions; and hence they are not repeatable. Models must be established individually and in real-time.

(4) This is not a data rich environment. At the starting time interval before substantial data become available one must rely on expert assessment to initiate the model and decision process. This implies that the modeling process must allow a seamless combination of assessment and data-generated estimation.

(5) Since data points are limited, low-complexity models and fast identification are always preferred.

(6) Due to medical constraints, the inputs are not allowed to be arbitrarily selected for best identification experiments or probing excitation.

These challenges, together with traditional focus of system identification on linear, well defined, and repeatable environment, have resulted in a gap between theoretical results in identification and applications to medical applications.

Patient Model Structures

In an attempt to understand the potential of system identification in this important application area, we have identified anesthesia decisions as a typical setting for studying the system identification problem. Some preliminary findings on the utility of Wiener model structures (Hammerstein models can be similarly applied), combination of assessment and real-time estimation, and identification algorithms are summarized below.

The goals of general anesthesia are to achieve hypnosis and analgesia simultaneously throughout a surgical operation while maintaining the vital functions of the body. One of the most critical tasks of anesthesia is to attain an adequate anesthetic depth.

The newly marketed BIS monitor provides a viable direct measurement of anesthesia depth. To facilitate control strategy development for improved anesthesia performance, it is highly desirable to develop representative models of BIS responses to drug infusion. Since patients differ dramatically in metabolism, pre-existing medical conditions, and surgical procedures, individualized models must be established for each patient with limited patient information and data points. A knowledge-based and control-oriented modeling approach was introduced recently and applied to develop a feedback and predictive control strategy for anesthesia infusion. The models retain only the key characteristics of patient responses that are essential for control strategy development and can be determined by either data or expert knowledge. Furthermore, an identification algorithm has been introduced for updating the patient model in real-time.

Due to complications in human metabolism and nerve systems, we do not perceive that the system dictates any specific model structure as especially superior. Simple model structures that can capture the key characteristics and maintain physiological meanings of model parameters will be preferable since they will allow easy interface with physicians and fast model updates.

As previously noted, we have tested the validity of Wiener structures in representing the patient dynamics. The patient dynamics is defined by three basic elements:

(1) Initial time delay $\tau_p$ after drug infusion;
(2) Time constant $T_p$ representing the speed of response;
(3) A nonlinear static function $f_p$ representing sensitivity of the patient to a drug dosage at steady state.

The meanings of these three components are depicted in FIGS. 2a and 2b.

This model structure can be mathematically represented by a Wiener model with input u and output y, $x=Gu+\tilde{w}$, $y=f(x)+\tilde{v}$ where G is a dynamic linear system, $f$ is a memoryless nonlinear function, and $\tilde{w}$ and $\tilde{v}$ are noises. x is an intermediate variable that cannot be directly measured. In our applications here, G and $f$ represent the transient and steady-state behavior of a patient's response to a drug infusion input, respectively. G can be discretized and represented by an ARMA model:

$$x_t = \phi_t^T \theta + \bar{w}_t$$

where $$\phi_t^T = [-x_{t-1}, \ldots, -x_{t-n}, u_t, \ldots, u_{t-n}], \theta^T = [a_1, \ldots, a_n, b_0, \ldots, b_n]$$

or approximated by a MA model with sufficiently high orders.

The sensitivity function $f$ can be modeled by either a linear combination of some pre-selected base functions or a parameterized nonlinear function. The delay time $\tau_p$, time constant $T_p$, and the sensitivity function $f$ vary greatly among patients and must be established individually for each patient.

To verify the utility of the model structure and develop individual patient models, clinical data are collected. One of these data sets is described below to illustrate the process and results. The anesthesia process was administered manually by an anesthesiologist and lasted about 76 minutes, starting from the initial drug administration and continuing until the last dose of administration.

To verify the capability of the model structure, the data were used to determine model parameters and function forms, by an off-line estimation method (an optimal nonlinear LS estimator). The actual response is compared with the model response over the entire surgical procedure. Comparison results are shown in FIG. 10a to 10d. Here, the inputs of drug titration (continuous drug flow) and bolus (drug injection of a short duration) are the recorded real-time data. The model captures the key trends and magnitudes of the output variations in the surgical procedure. This indicates that the model structure, though very simple, contains sufficient freedom in representing the main features of the patient response. Also, the impact of surgical stimulation is captured by the model.

Reliability Evaluation of Identification Algorithms

Despite well established theoretical results on many identification algorithms, our studies indicate that to enhance reliability of system identification in medical applications, some well developed algorithms must be significantly re-evaluated and modified beyond routine convergence analysis. Our criteria for evaluating an algorithm include:

(1) Accuracy and convergence (estimation errors);
(2) Robustness (error excursion frequencies);
(3) Model complexity (number of parameters);
(4) Time complexity (data points required); and
(5) Usage convenience (requirements of delicate tuning or sensitive dependence on initial values are not desirable).

To understand the reliability of various identification methods on Wiener models and anesthesia patient models, the following platforms are used as a benchmark.

Platform 1: A Simulated Wiener System

The example platform is expressed by the Wiener system:

$$x_t = a_1 u_t + a_2 u_{t-1} + w_t,$$

$$y_t = 2x_t + \frac{C_1 x_t (x_t - \xi_1)}{\xi_1(\xi_1 - \xi_2)} + \frac{C_2 x_t (x_t - \xi_2)}{\xi_2(\xi_2 - \xi_1)} + v_t$$

where the true parameters are $a_1=2$; $a_2=1$; $C_1=4.1$; $C_2=3.5$. The testing points for the expert information on the nonlinear function are $\xi_1=5$; $\xi_2=10$. For anesthesia applications, we always have $y_t=0$ when $x_t=0$. The nominal function $y_t=2x_t$ is known and contained in the expression. Prior information on unknown parameters are given by: range of $a_1=[0, 3]$; range of $a_2=[0, 2]$; range of $C_1=[2, 6]$; range of $C_2=[1, 5]$.

$w_t$ and $v_t$ are i.i.d. uniformly distributed random processes, in the range [−1.5, 1.5].

Platform 2: An Anesthesia Patient Model

Figure 19:
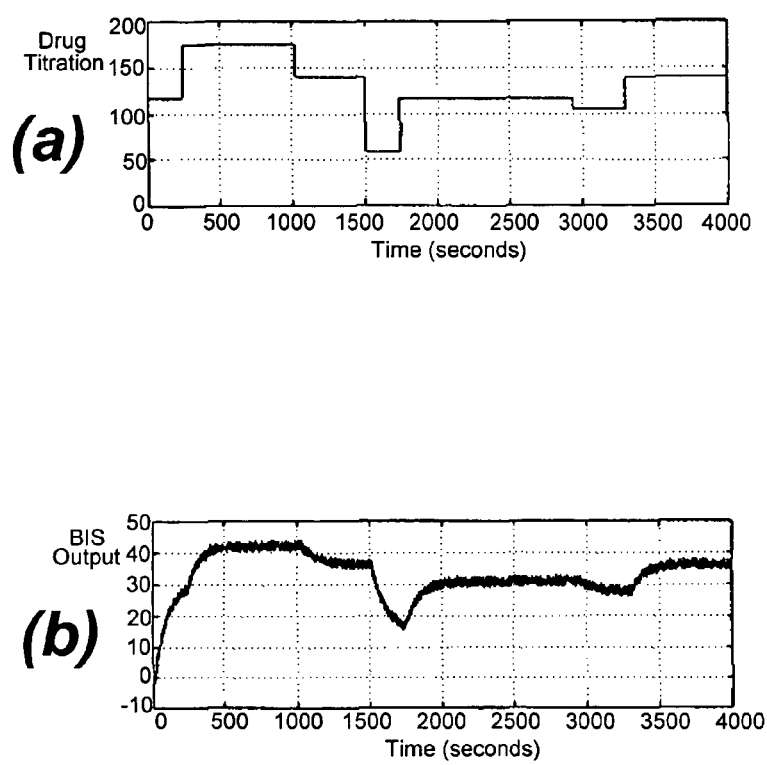
FIGS. 19a and 19b are graphical representations showing a patient's BIS response to propofol titration.
Figure 20:
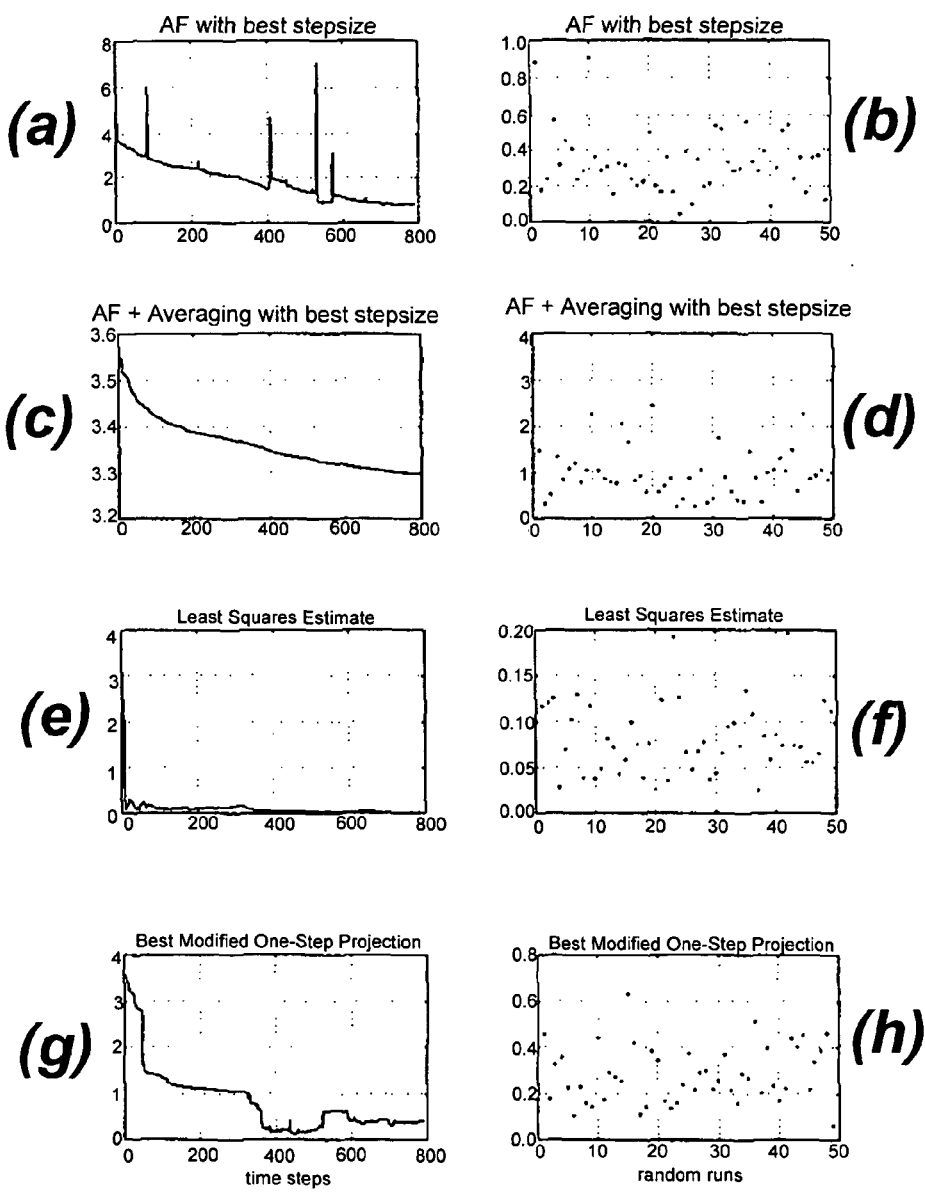
FIGS. 20a to 20h are graphical illustrations that demonstrates the comparisons between recursive algorithms.

From patient data, the titration model is first extracted by an off-line method. The method eliminates the impact of surgical stimulation and drug impact from bolus injection, and produces a BIS response of the drug propofol titration on the patient as shown in FIGS. 19a and 19b.

Recursive Algorithms

Model parameter updating algorithms must be used to estimate the parameters of the Wiener model, especially the linear dynamic part. There have been established many valid recursive algorithms in a wide variety of applications. Our objective here is to evaluate the accuracy and convergence of different recursive algorithms under this application. Here a linear system is used $$y_t = 1.5 y_{t-1} - 0.7 y_{t-2} + 0.9 u_{t-1} + 0.5 u_{t-2} + e_t = \phi_t^T \theta + e_t$$

where e is a Gaussian disturbance with zero mean and unit variance.

The evaluated algorithms include the following four types. For the first three algorithms, since the tunable parameters have dramatic impact on their performance, their values are optimized in each run.

(1) Adaptive Filtering $$\theta_{t+1} = \theta_t + \frac{c}{t^r} \phi_t (y_t - \phi_t^T \theta_t), 0 < r \le 1.$$

(2) Adaptive Filtering with Averaging $$\hat{\theta}_{t+1} = \theta_t + \frac{c}{t^r} \phi_t (y_t - \phi_t^T \hat{\theta}_t), 0 < r \le 1;$$

$$\theta_{t+1} = \theta_t - \frac{1}{t+1} \theta_t + \frac{1}{t+1} \hat{\theta}_{t+1}.$$

(3) One-step Modified Optimal Projection $$\theta_{t+1} = \theta_t + r \frac{\phi_t}{a + \phi_t^T \phi_t} (y_t - \phi_t^T \theta_t).$$

(4) Recursive Least Squares $$K_t = \frac{P_t \phi_t}{1 + \phi_t^T P_t \phi_t}; P_{t+1} = (I - K_t \phi_t^T) P_t;$$

$$\theta_{t+1} = \theta_t + K_t (y_t - \phi_t^T \theta_t).$$

The algorithms are started with the same initial estimate, which is obtained by using an LS estimate with 10 data points. Then the recursive algorithms are performed for 1000 data points. For each algorithm, the estimation errors during the last 20 time points are averaged. The averaged error is used as a measure of identification accuracy. The simulation is repeated 50 times. The 50 estimation errors are plotted in the right column of FIGS. 20a to 20h for algorithm comparison. Also, the 50th error trajectory for each algorithm is illustrated in the left column.

It seems clear that the recursive least squares algorithm outperforms the rest in two aspects: (1) It provides more accurate estimates; (2) It does not require any variable tuning. It is noted that we have optimized variables for each run in other algorithms. In real applications, these variables cannot be optimized over each sample path. Consequently, the actual performance of these algorithms will be worse than what we have demonstrated in this simulation. In fact, when the variables are fixed, we encountered occasionally parameter divergence in adaptive filtering or projection algorithms. In general, the RLS may require slightly more computational time. However, this is not an issue in this case since the model order is small in patient models. Consequently, we will use LS algorithms in our identification of patient models.

Block Recursion

A two-step recursive estimation algorithm has been proposed for identifying the patient model in real-time. The procedure can be briefly summarized as follows:

Two-step Procedure. We start at time k=0 with $\hat{\theta}_0$ (the parameters for the linear part) and $\Theta_0$ (the parameters for the nonlinear part).

Step 1: At time k, the available $\hat{\Theta}_0$ is used to map the output $y_k$ backwards to obtain the "intermediate" output $\hat{x}_k$. Then $u_k$ and $\hat{x}_k$ are used to update $\hat{\theta}_{k+1}$.

Step 2: From the obtained $\hat{\theta}_{k+1}$ we map $u_{k+1}$ forward to obtain $\hat{x}_{k+1}$. Then $\hat{x}_{k+1}$ and $y_{k+1}$ are used to update $\hat{\Theta}_{k+1}$ from $\hat{\Theta}_k$.

Selection of recursive algorithms, averaging, projection into a bounded set, step size selection, and convergence analysis have previously been presented. This algorithm is computationally very efficient.

To evaluate its reliability, a known system is used that works reasonably well when initial estimates are close to true values. However, when initial estimates are further away from true values the algorithm demonstrated irregular behavior that includes parameter divergence, slow parameter drifting, and large output prediction errors. In other words, it is not a reliable algorithm.

Figure 21:
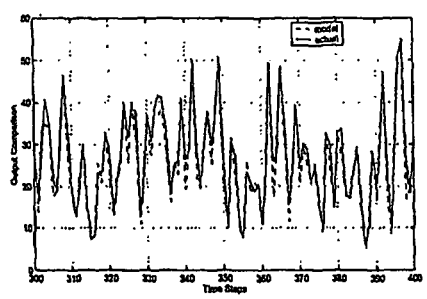
FIG. 21 is a graphical illustration that shows the result of block recursion of a simulation.

Consequently, the algorithm is modified into a block recursive algorithm. In this modified algorithm, the parameters are not updated upon receiving each observation. But rather, a block of m observations is used collectively to update the model parameters. Starting with the most recent estimate as an initial condition, the algorithm searches for the optimal parameters that minimize the output errors between the model output and measured output in the data block. This modified algorithm have shown a greatly improved reliability. For the system (2), we used the block size 10 to run a simulation of 800 data points with a random input. The simulation was repeated 50 times and demonstrated good prediction capability in each run. A typical result is shown in FIG. 21. On the other hand, parameter convergence is not always demonstrated.

Optimization Efficiency

For a nonlinear system, optimization carries potentially large computational burdens. As shown in the previous section, overly simplified algorithms may suffer loss of reliability. In search of efficient optimization methods during a block recursion, an embedded optimization method was employed. In this method, for given parameters of the nonlinear part of the model, the parameters of the linear part are optimized by the least squares algorithm that is computationally very simple. Consequently, only the parameters of the nonlinear function must be searched. In our evaluation, global grid search, local grid search (around the initial estimate), simplex optimization methods were tested. The simplex method finds similar parameter values but requires on average only about one twentieth of computational time required by the grid search methods.

Parameterization of Nonlinear Functions

The memoryless function $f$ in the Wiener model represents steady-state sensitivity: The impact of the input (drug amount) on the outcome. Theoretically, a memoryless and continuous nonlinear function can be approximated by a polynomial function to any degree of accuracy when the order of the polynomial is allowed to increase. However, the parameters of the polynomial usually do not carry any physical meaning. It has been proposed that the following functions are more suitable to connect with expert assessment.

A physician's knowledge can be expressed as follows: Given m typical x amounts $\xi_1, \ldots, \xi_m$, the approximate ranges of the predicted steady-state outcomes are $[\underline{y}_1, \overline{y}_1], \ldots, [\underline{y}_m, \overline{y}_m]$. We parameterize $f$ by:

$$y = f(x) = \sum_{i=1}^{M} C_i \Phi_i(X)$$

where $\Phi_i(x)$ is the $m^{th}$ order polynomial:

$$\Phi_i(x) = \frac{\prod_{j=1, j\neq i}^{m}(x - \xi_j)}{\prod_{j=1, j\neq i}^{m}(\xi_i - \xi_j)}$$

$\Phi_i(x)$ satisfies $\Phi_i(\xi_j)=0$, $j \neq i$; $\Phi_i(\xi_j)=1$. Consequently, the prior expert information becomes precisely the prior interval information on the parameters $\Theta=[C_1, \ldots, C_m]'$; $C_i \in [\underline{y}_i, \overline{y}_i]$, $i=1, \ldots, m$.

This knowledge will serve as the prior information on the unknown parameters $\theta$ and $\Theta$. Consequently, the parameters will have clear physical meanings and expert assessment can be integrated seamlessly into this parameterization.

Interestingly, for computational purposes this parameterization implies further complications. Understanding that the nonlinear function in this application represents a drug's steady-state impact on the patient outcome. Hence it must obey the basic monotone principle: the more the drug infusion rate, the more the impact on the patient. Unfortunately, this requirement is not naturally embedded in the polynomial parameterization. In fact, in a box of parameter values for the polynomials in the resulting nonlinear functions are not always monotone. Also, for the same parameters, the corresponding function may become non-monotone when the range of the drug rates is enlarged. Consequently, in search of optimal parameters during system identification, monotonicity must be laboriously checked in each evaluation and sometimes leads to the failure of a local search.

Figure 24:
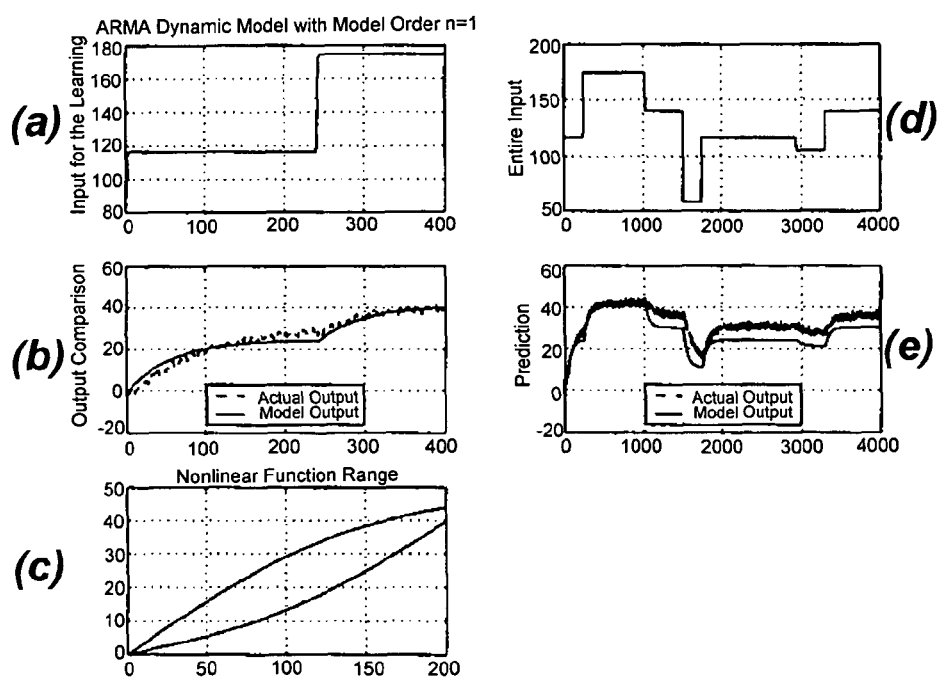
FIGS. 24a to 24c are graphical representations showing an Auto-Regression and Moving Average ("ARMA") model of order 1.
Figure 25:
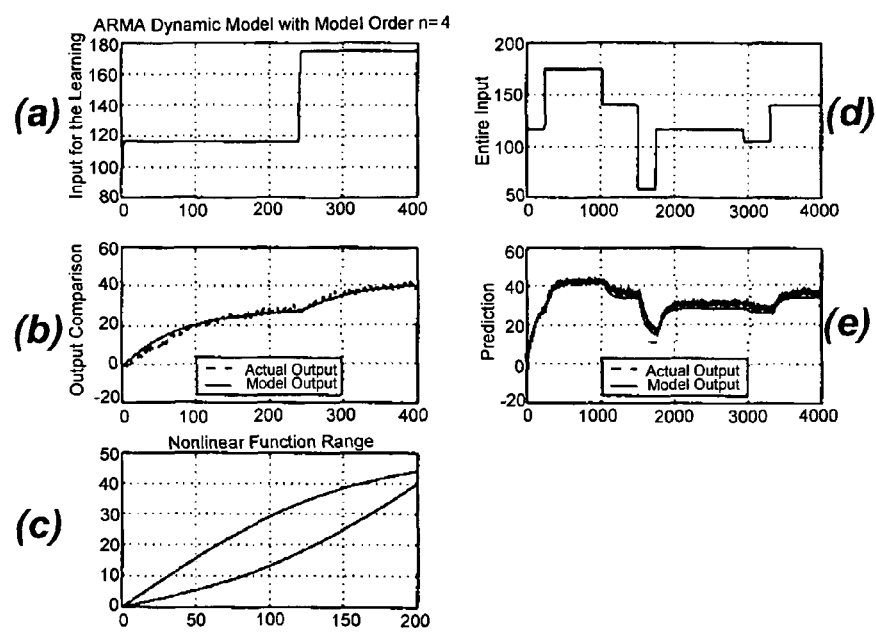
FIGS. 25a to 25e are graphical representations showing an ARMA model of order 40.
Figure 26:
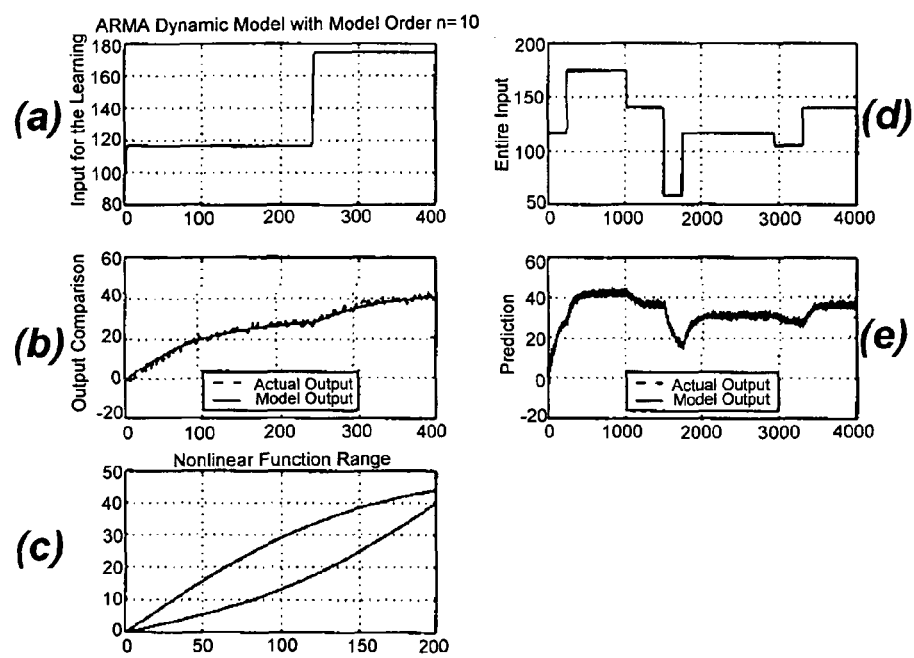
FIGS. 26a to 26e are graphical representations showing an ARMA model of order 10.

A remedy of this situation is found by using a different parameterization of the nonlinear function. The following two-parameter function is employed: Suppose that x takes values in [0,b].

$$y = r\left(x \pm \left(\frac{erf(\alpha x)}{erf(\alpha b)} - x\right)\right)$$

where $erf(\cdot)$ is the standard error function, and the parameters r and $\alpha$ define variation in y at x=b and curvatures of the erf function in $x \in [o,b]$. Since it is very simple to find a box in r-$\alpha$ space under which the resulting nonlinear functions are always monotone, it greatly improves time complexity in search algorithms. In FIGS. 24, 25, and 26, the ranges of searched nonlinear functions are included in the bottom plots.

Model Complexity and Time Complexity

Model complexity and time complexity are especially important in medical applications due to limited data points, input probing richness, requirements of prompt decisions, and time varying natures of patient models. In this evaluation the patient model in FIGS. 19a and 19b is used. Since actual model order and structures are unknown to the designer, we simply use either MA or ARMA models of various orders and evaluate their prediction capability. The input data are the real drug infusion rates which do not provide much richness in excitation. The total surgery lasted about 4000 seconds. We used the first 400 seconds of the data for system identification for ARMA models, and 1000 data points for MA models since their orders are much higher. Then the prediction capability of the identified model is evaluated by applying it to the entire data. It is noted that during the first 400 seconds, the input changes its value only once.

Figure 22:
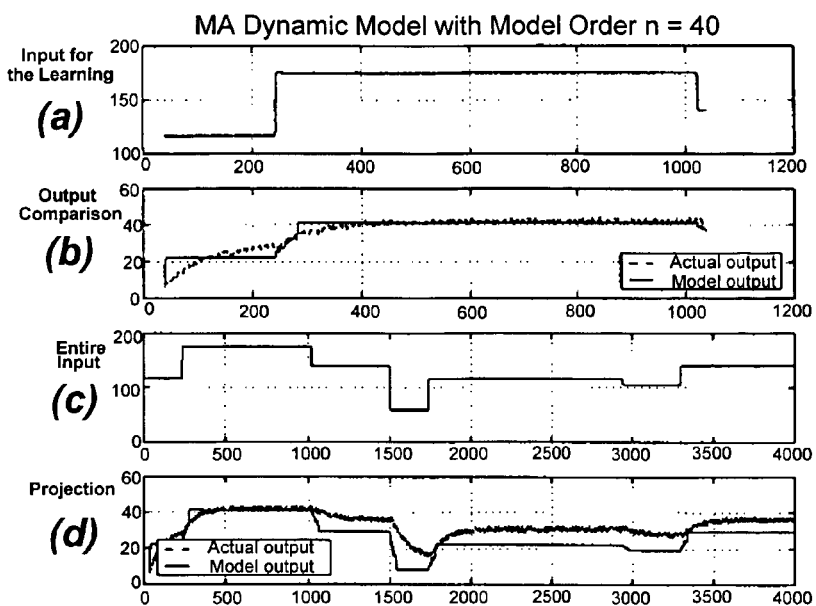
FIGS. 22a to 22d are graphical representations showing a moving average model of order 40.
Figure 23:
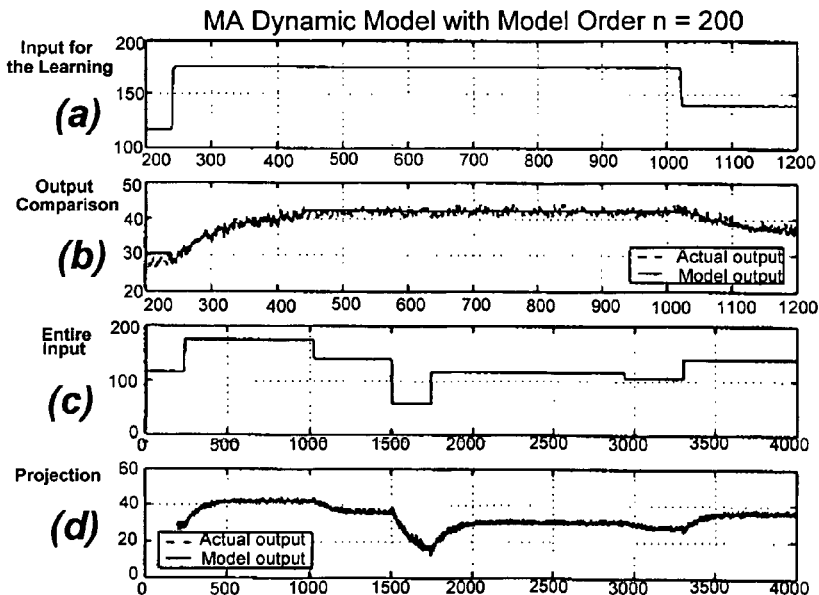
FIGS. 23a to 23d are graphical representations showing a moving average model of order 200.

Conceptually, it is arguable that for a linear stable system, it is always possible to approximate it by a FIR model (moving average). This model structure can significantly simplify theoretical analysis. However, a comparison of FIGS. 22 and 23 shows clearly that to capture the dynamics of the actual system, the order of the MA model must be very high. This is highly undesirable in this application since 200 parameters in this model is a very high model complexity. It also increases identification time complexity. Since an overall patient model contains many model blocks of similar types, the MA structure will imply a very large parameter set for system identification when the overall system is considered.

FIGS. 24, 25, and 26 show the prediction capability of ARMA models of orders 1, 4 and 10, respectively. It is seen that ARMA models can capture the dynamics of the system with much lower orders than MA models.

In sum, it is noted that: (1) Wiener or Hammerstein models have great potential utility in modeling patient dynamics; (2) Reliable identification is a stringent requirement that mandates a modified evaluation criterion on identification algorithms; (3) Within the framework of reliable identification, all components of a system identification must be carefully examined in terms of robustness, reliability, model complexity, time complexity, accuracy, and tracking capability for time varying parameters.

Although the invention has been described in terms of specific embodiments and applications, persons skilled in the art may, in light of this teaching, generate additional embodiments without exceeding the scope or departing from the spirit of the claimed invention. Accordingly, it is to be understood that the drawing and description in this disclosure are proffered to facilitate comprehension of the invention and should not be construed to limit the scope thereof.

What is claimed is:

1. An apparatus for assisting a human expert during the administration of a medical anesthesia drug to a patient, the apparatus comprising:
a computing machine having:
an input that receives data corresponding to a plurality of coefficients $C_1$, $C_2$, $C_3$, as well as time periods $\tau_p$ (initial time delay after infusion of the anesthesia drug) and $T_p$ (time constant representing speed of response), the time periods being initially determined in response to an assessment of the patient by the human expert;
a memory that stores the plurality of coefficients $C_1$, $C_2$, $C_3$, and the time periods $\tau_p$ and $T_p$;
a processor that solves the formula:

$$y = f_P(x) = C_1 \frac{x}{x_1} \Phi_1(x) + C_2 \frac{x}{x_2} \Phi_2(x) + C_3 \frac{x}{x_3} \Phi_3(x)$$

and
a display that displays resulting data to the human expert.

2. The apparatus of claim 1, where a relative value between 1 and 10 is assigned to represent the patient's response to infusion of the anesthesia drug, where 1 represents the slowest and 10 represents the fastest, and the memory of the computing machine is configured to store the relative value.

3. The apparatus of claim 1, wherein typical set points are selected to be $x_1 \cong 50$, $x_2 \cong 100$, and $x_3 \cong 150$, and are stored in the memory of the computing machine.

4. A method of using a computing machine to assist a human expert in the administration of anesthesia to a patient, the computing machine having a memory to determine a model that corresponds to a predicted response of the patient to anesthesia drug delivery, the method comprising the steps of:
determining an initial time delay $\tau_p$ after drug infusion for the patient;
entering a time delay value corresponding to the initial time delay $\tau_p$ into the memory of the computing machine;
determining a time constant $T_p$ representing speed of response of the patient;
entering a time constant value corresponding to the time constant $T_p$ into the memory of the computing machine;
determining a nonlinear static function $f_p$ representing the sensitivity of the patient to a dosage of the anesthesia drug at steady state; and
displaying data corresponding to a solution of the formula:

$$y = f_P(x) = C_1 \frac{x}{x_1} \Phi_1(x) + C_2 \frac{x}{x_2} \Phi_2(x) + C_3 \frac{x}{x_3} \Phi_3(x).$$

5. The method of claim 4, wherein said steps of determining an initial time delay $\tau_p$, determining a time constant $T_p$, and determining a nonlinear static function $f_p$, are implemented in a Weiner structure that is computed in the computing machine.

6. The method of claim 4, wherein said steps of determining an initial time delay $\tau_p$, determining a time constant $T_p$, and determining a nonlinear static function $f_p$, are implemented in a Hammerstein structure that is computed in the computing machine.

7. Apparatus for determining a predicted response of a patient to the administration of an anesthesia drug, the apparatus comprising:
a first memory for storing patient dynamics information relating to the infusion of a bolus dosage of anesthesia drug, said first memory having a first output for producing a first output signal corresponding to a first anesthesia level;
a second memory for storing patient dynamics information relating to the infusion of a titrated dosage of anesthesia drug, said second memory having a second output for producing a second output signal corresponding to a second anesthesia level;
a third memory for storing patient dynamics information relating to the patient's predicted response to events of surgical stimulation, said third memory having a third output for producing a third output signal corresponding to an anesthesia effect level;
a signal combiner arrangement for receiving the first and second output signals and the anesthesia effect level, and producing at an output thereof a combined anesthesia effect signal;
a limiter coupled to the output of said signal combiner for establishing maximum and minimum values of the combined anesthesia signal;
a processor for generating a virtual anesthesia monitor that produces an anesthesia value responsive to the combined anesthesia signal; and
a display that displays resulting data.

8. The apparatus of claim 7, wherein the first and second anesthesia levels correspond to respective bi-spectrum levels of the patient's electroencephalogram signal, the anesthesia effect level is a bi-spectrum level, and the combined anesthesia signal is a combined bi-spectrum level signal.

9. The apparatus of claim 8, wherein the virtual anesthesia monitor is a virtual bi-spectrum monitor for producing a bi-spectrum value responsive to the combined bi-spectrum signal.

10. The apparatus of claim 7, wherein there is further provided a source of known noise to compensate for an unpredictable disturbances signal, and said signal combiner arrangement is arranged to receive the unpredictable disturbances signal and the combined anesthesia effect signal is responsive to the unpredictable disturbances signal.

\* \* \* \* \*